United States Patent
Van Criekinge et al.

(10) Patent No.: US 9,605,312 B2
(45) Date of Patent: Mar. 28, 2017

(54) METHODS OF DETECTING MUTATIONS IN BRAF AND EPIGENETIC CHANGES

(71) Applicant: MDxHealth SA, Sart-Tilman (Liege) (BE)

(72) Inventors: Wim Van Criekinge, Waarloos (BE); James Clark, Liege (BE); Johan Vandersmissen, Hoeselt (BE)

(73) Assignee: MDxHealth, SA, Sart-Tilman (Liege) (BE)

( * ) Notice: Subject to any disclaimer, the term of this patent is extended or adjusted under 35 U.S.C. 154(b) by 0 days.

(21) Appl. No.: 14/363,182

(22) PCT Filed: Dec. 6, 2012

(86) PCT No.: PCT/IB2012/003094
§ 371 (c)(1),
(2) Date: Jun. 6, 2014

(87) PCT Pub. No.: WO2013/084075
PCT Pub. Date: Jun. 13, 2013

(65) Prior Publication Data
US 2014/0322714 A1     Oct. 30, 2014

Related U.S. Application Data

(60) Provisional application No. 61/567,496, filed on Dec. 6, 2011.

(51) Int. Cl.
*C12Q 1/68*     (2006.01)

(52) U.S. Cl.
CPC ......... *C12Q 1/6881* (2013.01); *C12Q 1/6858* (2013.01); *C12Q 1/6886* (2013.01); *C12Q 2600/154* (2013.01); *C12Q 2600/156* (2013.01)

(58) Field of Classification Search
None
See application file for complete search history.

(56) References Cited

U.S. PATENT DOCUMENTS

2006/0194208 A1* 8/2006 Tetzner ............... C12Q 1/6886
                                                                      435/6.12
2011/0104663 A1* 5/2011 Tetzner ........................... 435/6

FOREIGN PATENT DOCUMENTS

| EP | 1746169 | 1/2007 |
|---|---|---|
| EP | 2309005 | 4/2011 |
| WO | 0162064 | 8/2001 |
| WO | 2008084219 | 7/2008 |

OTHER PUBLICATIONS

Koinuma et al. Int. J. Cancer. 2004. 108: 237-242.*
Karpinski et al Mol Cancer Res. 2008. 6(4): 585.*
Deng et al., "Simultaneous detection of CpG methylation and single nucleotide polymorphism by denaturing high performance liquid chormatography", Nucleic Acids Research, Feb. 1, 2002, 30(3):13e.
Ogino et al., "MGMT germline polymorphism is associated with somatic MGMT promoter methylation and gene silencing in colorectal cancer", Aug. 11, 2007, Carcinogenesis, 28(9):1985-1990.
International Search Report for PCT/IB2012/003094 dated Jun. 11, 2013.
Written Opinion for PCT/IB2012/003094 dated Jun. 11, 2013.
International Preliminary Report on Patentability for PCT/IB2012/003094 dated Jun. 19, 2014.

* cited by examiner

*Primary Examiner* — Carla Myers
(74) *Attorney, Agent, or Firm* — Andrus Intellectual Property Law, LLP

(57) ABSTRACT

Disclosed are methods for assessing the methylation and mutation status of nucleic acid in a sample. The methods provide for methylation-dependent modification of the nucleic acid in a sample, and subsequently nucleic acid amplification processes to distinguish between mutated and non-mutated target sequence.

14 Claims, 38 Drawing Sheets

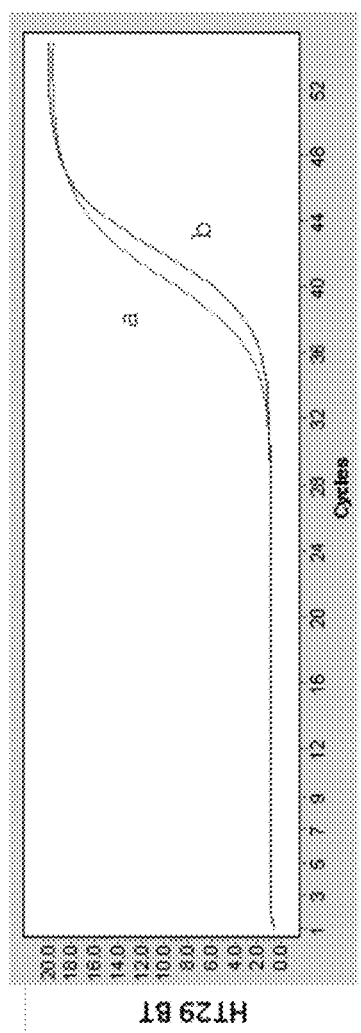
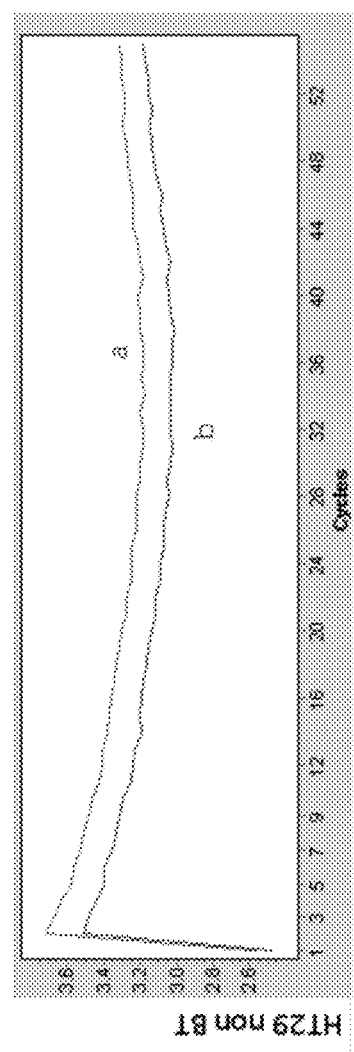
Figure 1 A
Figure 1 B

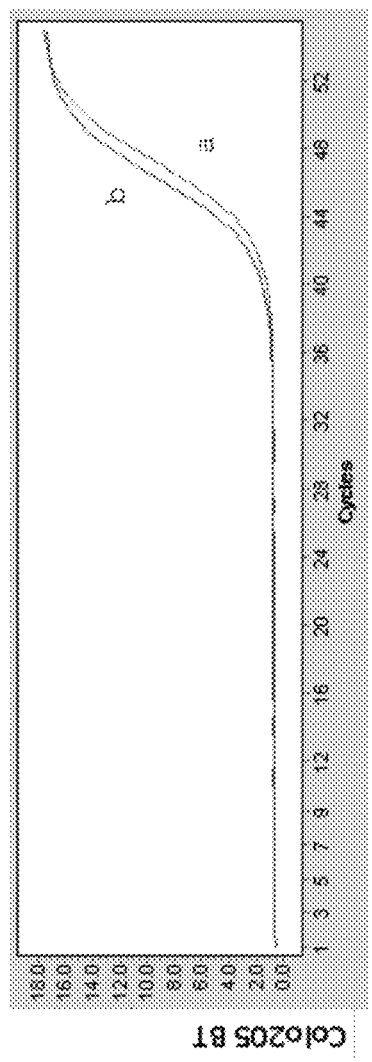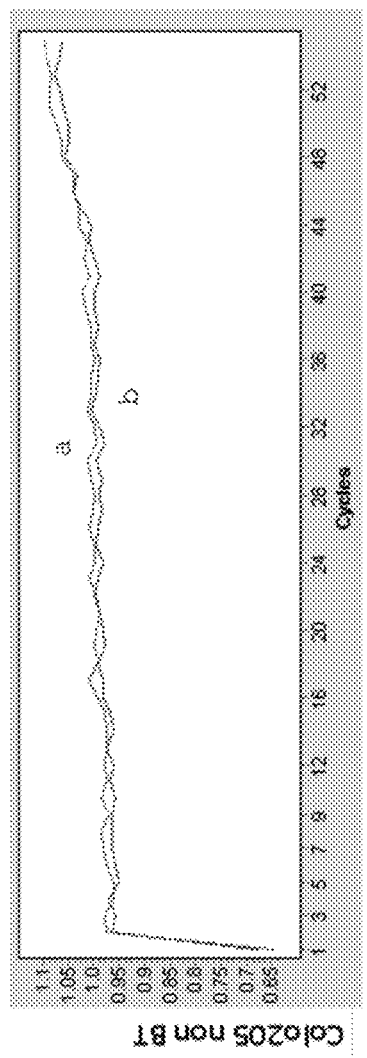

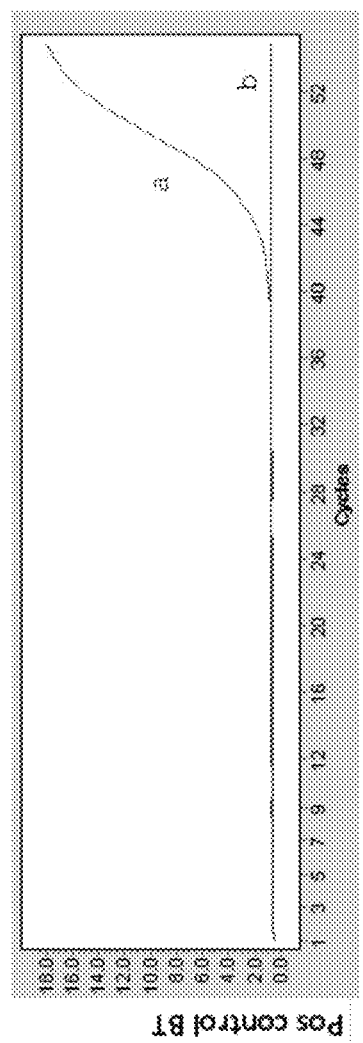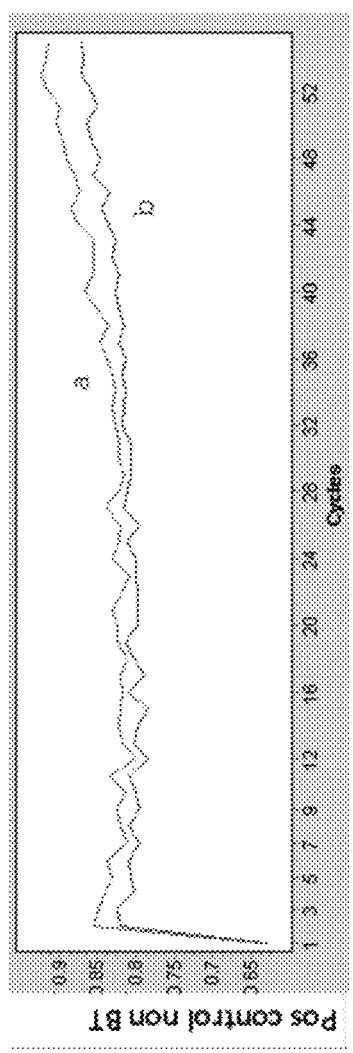
Figure 3 A
Figure 3 B

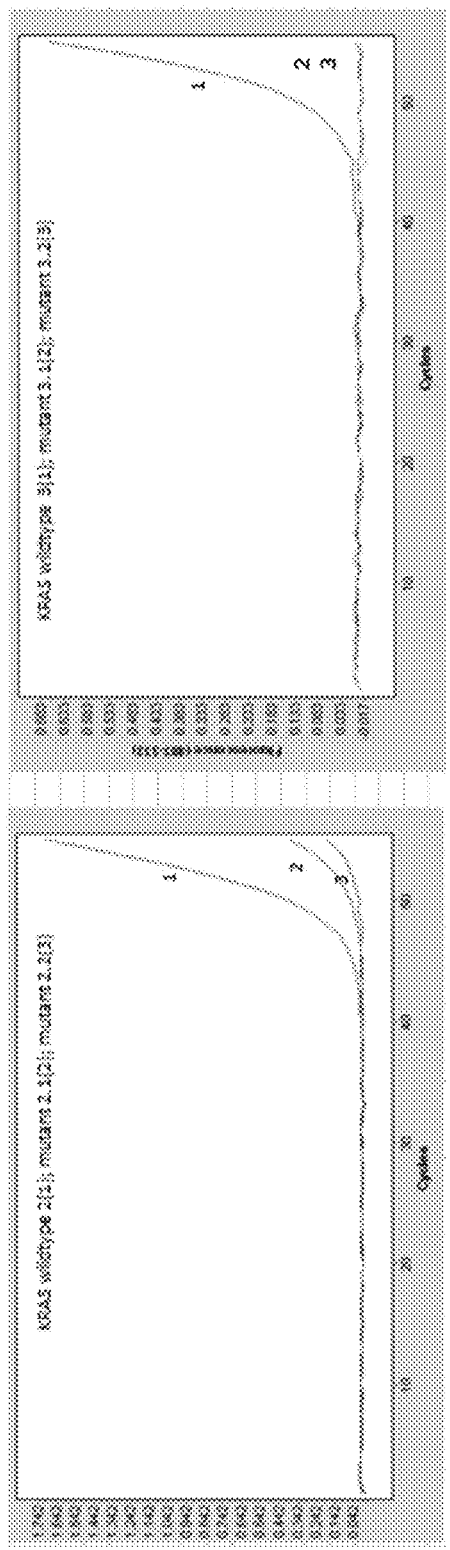
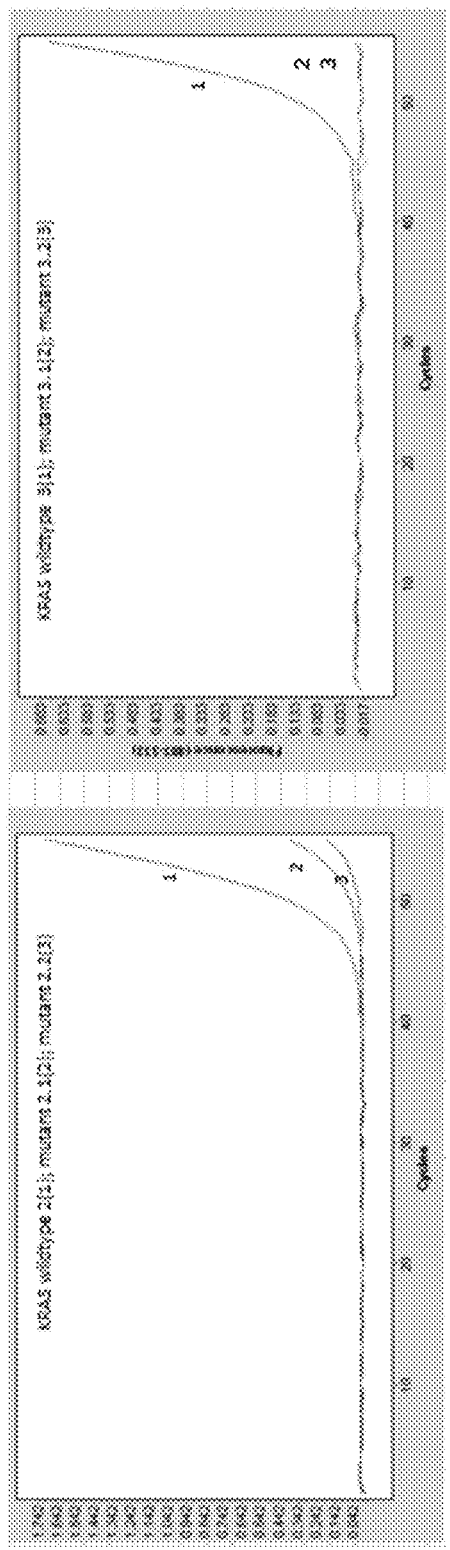
Figure 6 A
Figure 6 B

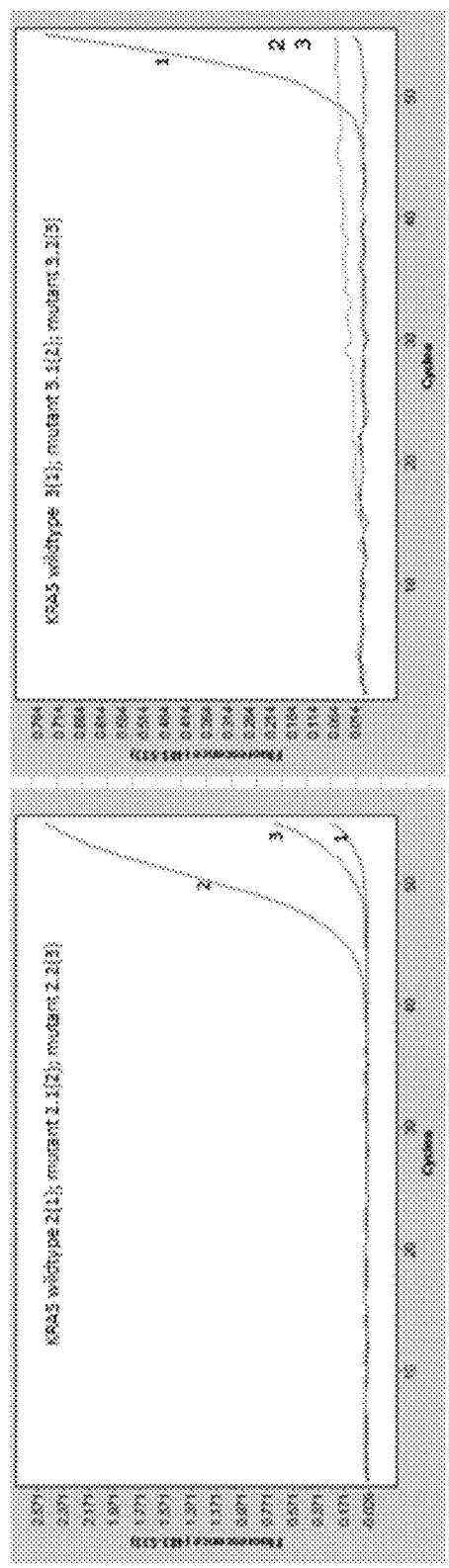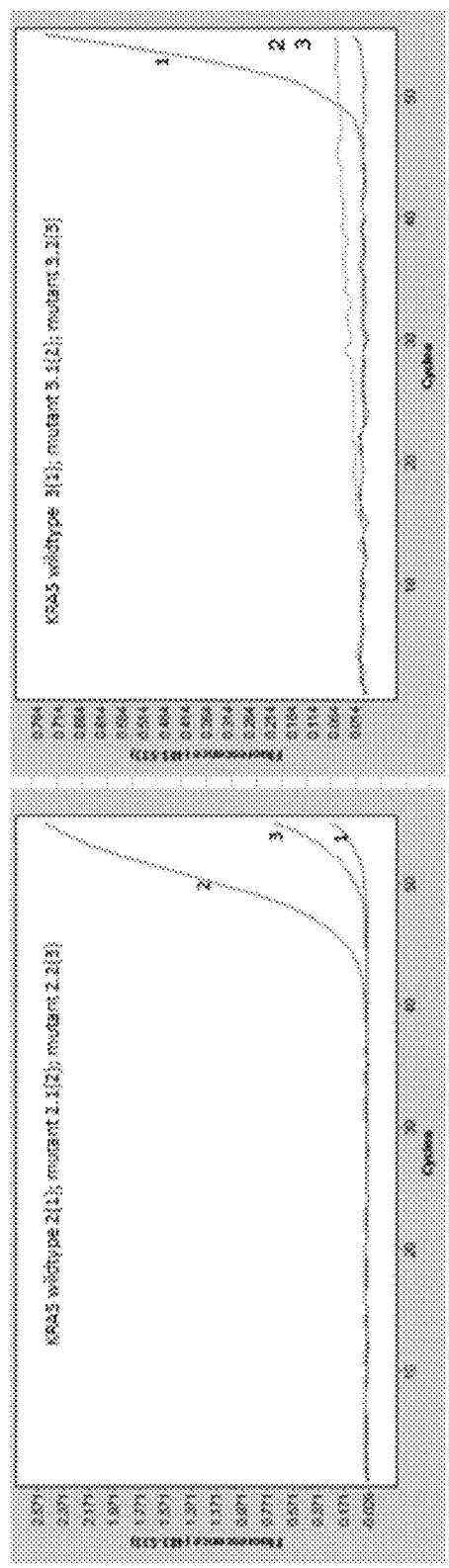
Figure 14 A
Figure 14 B

SEQUENCE LISTING

```
<160> NUMBER OF SEQ ID NOS: 16

<210> SEQ ID NO 1
<211> LENGTH: 50
<212> TYPE: DNA
<213> ORGANISM: Artificial
<220> FEATURE:
<223> OTHER INFORMATION: Oligonucleotide primer for amplifying human
      BRAF gene

<400> SEQUENCE: 1
```
cttcataaaa acctcacaat aaaaataaat aattttaatc taactacaat        50

<210> SEQ ID NO 2
<211> LENGTH: 42
<212> TYPE: DNA
<213> ORGANISM: Artificial
<220> FEATURE:
<223> OTHER INFORMATION: Oligonucleotide primer for amplifying human
      BRAF gene

<400> SEQUENCE: 2
agtagtattt tagggttaaa aatttaatta gtggaaaaat ag        42

<210> SEQ ID NO 3
<211> LENGTH: 50
<212> TYPE: DNA
<213> ORGANISM: Artificial
<220> FEATURE:
<223> OTHER INFORMATION: Oligonucleotide primer for amplifying human
      BRAF gene

<400> SEQUENCE: 3
cttcataaaa acctcacaat aaaaataaat aattttaatc taactacaaa        50

<210> SEQ ID NO 4
<211> LENGTH: 44
<212> TYPE: DNA
<213> ORGANISM: Artificial
<220> FEATURE:
<223> OTHER INFORMATION: Oligonucleotide primer for amplifying human
      KRAS gene

<400> SEQUENCE: 4
tttgttgaaa atgattgaat ataaatttgt ggtagttgga gttg        44

<210> SEQ ID NO 5
<211> LENGTH: 44
<212> TYPE: DNA
<213> ORGANISM: Artificial
<220> FEATURE:
<223> OTHER INFORMATION: Oligonucleotide primer for amplifying human
      KRAS gene

<400> SEQUENCE: 5
tttgttgaaa atgattgaat ataaatttgt ggtagttgga gtta        44

<210> SEQ ID NO 6
<211> LENGTH: 42
<212> TYPE: DNA
<213> ORGANISM: Artificial
<220> FEATURE:
<223> OTHER INFORMATION: Oligonucleotide primer for amplifying human
      KRAS gene

<400> SEQUENCE: 6
gaaaatgatt gaatataaat tgtggtagt tggagttggt gg        42

<210> SEQ ID NO 7
<211> LENGTH: 42
<212> TYPE: DNA
<213> ORGANISM: Artificial
<220> FEATURE:
<223> OTHER INFORMATION: Oligonucleotide primer for amplifying human
      KRAS gene

<400> SEQUENCE: 7
gaaaatgatt gaatataaat ttgtggtagt tggagttggt gt        42

<210> SEQ ID NO 8
<211> LENGTH: 42
<212> TYPE: DNA
<213> ORGANISM: Artificial
<220> FEATURE:
<223> OTHER INFORMATION: Oligonucleotide primer for amplifying human
      KRAS gene

<400> SEQUENCE: 8
gaaaatgatt gaatataaat tgtggtagt tggagttggt ga        42

<210> SEQ ID NO 9
<211> LENGTH: 45
<212> TYPE: DNA
<213> ORGANISM: Artificial
<220> FEATURE:
<223> OTHER INFORMATION: Oligonucleotide primer for amplifying human
      KRAS gene

<400> SEQUENCE: 9
tttgttgaaa atgattgaat ataaatttgt ggtagttgga gttgg        45

<210> SEQ ID NO 10
<211> LENGTH: 45
<212> TYPE: DNA
<213> ORGANISM: Artificial
<220> FEATURE:
<223> OTHER INFORMATION: Oligonucleotide primer for amplifying human
      KRAS gene

<400> SEQUENCE: 10
tttgttgaaa atgattgaat ataaatttgt ggtagttgga gttga        45

<210> SEQ ID NO 11
<211> LENGTH: 45
<212> TYPE: DNA
<213> ORGANISM: Artificial
<220> FEATURE:
<223> OTHER INFORMATION: Oligonucleotide primer for amplifying human
      KRAS gene

<400> SEQUENCE: 11
tttgttgaaa atgattgaat ataaatttgt ggtagttgga gttgt        45

<210> SEQ ID NO 12
<211> LENGTH: 40
<212> TYPE: DNA
<213> ORGANISM: Artificial
<220> FEATURE:
<223> OTHER INFORMATION: Oligonucleotide primer for amplifying human
      KRAS gene ne

<400> SEQUENCE: 12
cctacaccaa taatatacat attaaaacaa aatttacctc        40

<210> SEQ ID NO 13
<211> LENGTH: 18
<212> TYPE: DNA
<213> ORGANISM: Artificial
<220> FEATURE:
<223> OTHER INFORMATION: Oligonucleotide primer for amplifying human
      P16 gene

<400> SEQUENCE: 13
ttaggtaagg ggacgtcg        18

```
<210> SEQ ID NO 14
<211> LENGTH: 21
<212> TYPE: DNA
<213> ORGANISM: Artificial
<220> FEATURE:
<223> OTHER INFORMATION: Oligonucleotide primer for amplifying human
      P16 gene

<400> SEQUENCE: 14
accacattcg ctaaatactc g                                              21

<210> SEQ ID NO 15
<211> LENGTH: 26
<212> TYPE: DNA
<213> ORGANISM: Artificial
<220> FEATURE:
<223> OTHER INFORMATION: Oligonucleotide primer for amplifying human
      beta-actin gene

<400> SEQUENCE: 15
tagggagtat ataggttggg gaagtt                                         26

<210> SEQ ID NO 16
<211> LENGTH: 27
<212> TYPE: DNA
<213> ORGANISM: Artificial
<220> FEATURE:
<223> OTHER INFORMATION: Oligonucleotide primer for amplifying human
      beta-actin gene

<400> SEQUENCE: 16
aacacacaat aacaaacaca aattcac                                        27
```

METHODS OF DETECTING MUTATIONS IN BRAF AND EPIGENETIC CHANGES

CROSS REFERENCE TO RELATED APPLICATION

The present application is the U.S. national stage of International Application PCT/IB2012/003094, filed Dec. 6, 2012, which international application was published on Aug. 22, 2013, as International Publication No. WO2013/084075. The International Application claims priority to U.S. Provisional Patent Application No. 61/567,496, filed Dec. 6, 2011, the contents of which are incorporated herein by reference in their entireties.

FIELD OF THE INVENTION

The present invention is concerned with the diagnosis and treatment of disease. The invention relates to methods and kits for diagnosing and treating a disease based upon detecting mutations and epigenetic modifications, typically in specific genes. The methods and kits permit the detection of a methylation status and mutations in bisulfite-treated nucleic acids, with the combined tests proving particularly advantageous in predictive profiling for drugs.

BACKGROUND OF THE INVENTION

Inappropriate function of genes can be caused by errors introduced into the genetic code itself or by faulty epigenetic mechanisms deciding which genes can or cannot be expressed. Failure to produce proteins in the correct amounts or at all can disrupt essential metabolic, regulatory or signalling pathways resulting in the development of disease.

A disease such as cancer is caused by failure of checks and balances that control cell growth and proliferation. Improper levels of transcription and translation of certain genes results in unregulated cell growth. Certain specific genetic mutations have been identified as linked to several types of cancer, and, for some cancer types, this information has been converted into clinical tests. (Casey et al., Hum Mol Genet. 1993 November; 2(11); 1921-7). Genetic variability is also one of the best documented causes in the inconsistency of tumor responses. For instance, it has been documented that KRAS mutations cause resistance to epidermal growth factor receptor (EGFR)-targeted therapy (Rizzo, Cancer Treatment Reviews. 2010).

Studies have demonstrated that alterations in DNA methylation can also cause cancer. DNA methylation is a chemical modification of DNA performed by enzymes called methyltransferases, in which a methyl group (m) is added to certain cytosines (C) of DNA. This non-mutational (epigenetic) process (mC) is a critical factor in gene, expression regulation. In normal cells, methylation occurs predominantly in regions of DNA that have few CG base repeats, while CpG islands, regions that have long repeats of CG bases, remain non-methylated. Aberrant methylation of CpG islands may cause transcriptional inactivation or silencing of expression of certain genes in human cancers (Okino et al., Molecular carcinogenesis 2007 October; 46(10):839-46). Assessing the methylation status of genes may help predicting a person's prognosis to cancer. It has also been shown that aberrant DNA methylation may affect the sensitivity of cancers to antineoplastic agents by altering expression of genes critical to drug response. A well-known example in humans is promoter hypermethylation of O(6)-methylguanine-DNA methyltransferase (MGMT), which predicts favorable outcome for glioblastoma patients treated with the alkylating agent temozolomide (Hegi, ClinCancerRes, 2004; Stupp, Lancet, 2009).

Specific gene mutations and altered methylation patterns have also been linked to the development of neurological, neurodegenerative diseases and cardiovascular disorders. For example, Patients with Rett syndrome have neurodevelopmental defects associated with mutations in MeCP2, that binds to methylated DNA. Other mutations such as those in the Presenilin 1 (PSEN1) gene, seem to represent the most common cause of monogenic Alzheimer Disease (Borroni et al., Neurol Sci. 2011 Aug. 6.). Neurodegenerative disorders such as Alzheimer (Mastroeni D et al., PLoS ONE. 2009; 4(8):e6617) and psychiatric disorders such as schizophrenia (Costa E et al. Expert Rev Neurother. 2009; 9(1):87-98) and depression (Deutsch S I et al., Clin Neuropharmacol. 2008; 31(2): 104-119) appear to have disease-specific methylation patterns as well. Abnormally methylated genes (Mastronardi F G et al., J Neurosci Res. 2007; 85(9):2006-2016.) have also been linked to multiple sclerosis. Additionally, DNA methylation was also found to be linked to several cardiovascular-related biomarkers, including homocysteine (Ingrosso D et al., Lancet. 2003; 361:1693-1699.) and C-reactive protein.

Mutated genes or genes with altered methylation patterns involved in key pathways can affect disease progression and have the potential to influence drug resistance and clinical outcome following therapy. Knowledge on both molecular events may allow a clinician to predict more accurately how a disease is likely to respond to specific therapeutic treatments. Sequence specific amplification techniques have been developed for detection of sequence variations and alterations of wild-type locus. In standard PCR and sequencing reactions, information about mC and other covalent base modifications in genomic DNA is lost. As a consequence, indirect methods for DNA methylation analysis that after the genomic DNA in a methylation-dependent manner before amplification have been developed. Many methods that investigate DNA methylation use bisulfite treatment (Frommer, M., et al., Proc Natl Acad Sci USA 89 (1992) 1827-31). Bisulfite attaches itself to the C-6 of the cytosine ring. Subsequently, under alkaline conditions, the sulfonated cytosine is deaminated and desulfonated to uracil. The presence of a methyl group at the C-5 position prevents sulfonation and, therefore, methylcytosine remains the same. The bisulfite treated sequence can subsequently be assessed by a number of different methods such as bisulfite genomic sequencing (Grigg, G., et al., Bioesssays 16 (1994) 431-6; Grigg, G. W., DNA Seq 6 (1996) 189-98), nucleotide extension assays (MS-SNuPE), Pyrosequencing, Methylation Specific PCR (U.S. Pat. No. 5,786,146), MethyLight (WO 00/70090) and HeavyMethyl (WO 02/072880).

Bisulfite conversion is confronted with certain limitation such as incomplete conversion. The conditions necessary for complete conversion, such as long incubation times, elevated temperature, and high bisulfite concentration, can lead to the degradation of about 90% of the incubated DNA (Grunau C et al., 2001. Nucleic Acids Res. 29 (13): E65-5). Consequently, bisulfite conversion is applied only when required, for instance for methylation status determination.

Both mutation and methylation are involved in disease development and in patients' responses to particular drugs, and thus it is suitable to target multiple DNA alterations (Park et al., Int. 2006 J. Cancer: 120, 7-12). Since mutation and methylation detection methods operate according to two different principles, they do not lend themselves to be combined in a single assay. The method detecting mutations employs genomic DNA as a target, whereas the method detecting methylation requires bisulfite treatment. Accordingly, simultaneous mutation and methylation assessment currently requires the steps of splitting a nucleic acid sample in two parts and treating one part with bisulfite in order to allow methylation detection. This splitting is time consuming and has a negative effect on the efficiency of the process. Also, clinical samples are often small and splitting samples becomes often an issue.

Thus, there appears to be a need for improved diagnostic assays cancer using reliable and reproducible methods for determining DNA methylation and DNA mutation patterns simultaneously. This invention was made to address the foregoing need.

SUMMARY OF THE INVENTION

The present invention provides a rapid method for assessing the methylation and mutation status of nucleic acid in a sample. The invention provides for methylation-dependent modification of the nucleic acid in a sample, and subsequently uses nucleic acid amplification processes to distinguish between mutated and non-mutated target sequence. In contrast to previous methods, the presence of a mutated or non-mutated target sequence is detected in a converted nucleic acid, allowing combined mutation and methylation detection in the same sample. Thus, the present invention eliminates the need of splitting the sample, inherent in previous PCR-based methods applied for simultaneous mutation and methylation assessment, and allows multiplexing targets.

Accordingly, the present invention provides a method for detecting the presence and/or amount of at least one mutated or non-mutated target sequence of interest in a DNA-containing sample, comprising:
(a) contacting the DNA-containing sample with a modifying reagent which selectively modifies non-methylated cytosine residues in the DNA to produce detectable modified residues but which does not modify methylated cytosine residues,
(b) amplifying the at least one mutated or non-mutated target sequence following treatment with the reagent,
(c) detecting the mutation status of the at least one target sequence,
wherein the presence and/or amount of mutation of the at least one target sequence is indicative of disease or predisposition to disease, or is indicative for response to a particular treatment with a drug or therapy.

The present invention also provides a method for detecting the presence and/or amount of a mutated or non-mutated first target sequence and of a methylated or non-methylated second target sequence of interest in a DNA-containing sample, comprising:
(a) contacting the DNA-containing sample with a modifying reagent which selectively modifies non-methylated cytosine residues in the DNA to produce detectable modified residues but which does not modify methylated cytosine residues,
(b) amplifying the mutated or non-mutated first target and the methylated or non-methylated second target sequences following treatment with the reagent,
(c) detecting the mutation status of the first target sequence and the methylation status of the second target sequence, wherein the presence and/or amount of methylation or mutation of the target sequences is indicative of disease or predisposition to disease, or is indicative for response to a particular treatment with a drug or therapy.

The methods of the present invention can be used for detecting a predisposition to, or the incidence of, disease, monitoring treatment of disease, predicting the likelihood of resistance/successful treatment of disease, selecting a suitable treatment regimen for disease, or selecting patients for treatment;

The invention also relates to a kit for detecting the presence and/or amount of at least one mutated or non-mutated target sequence of interest in a DNA-containing sample, comprising means for detecting at least a mutated or non-mutated target sequence in the sample following treatment with a modifying reagent, wherein detection of the mutation is indicative of disease or predisposition to disease, or is indicative for response to a particular treatment with a drug or therapy.

A kit for detecting the presence and/or amount of a mutated or non-mutated first target sequence and of a methylated or non-methylated second target sequence in a sample of interest comprising:
(a) means for detecting a mutation in the DNA contained within the sample following treatment with a modifying reagent, wherein detection of the mutations is indicative of disease or predisposition to disease, or is indicative for response to a particular treatment with a drug or therapy. and
(b) means for detecting the presence of methylation in the DNA contained within the sample following treatment with a modifying reagent, wherein detection of the methylation is indicative of disease, or predisposition to disease, or is indicative for response to a particular treatment with a drug or therapy.

Also provided is a kit for any of:
(a) detecting a predisposition to, or the incidence of, disease in a sample
(b) monitoring treatment of disease
(c) predicting the likelihood of successful treatment of disease
(d) predicting the likelihood of resistance to treatment of disease
(e) selecting a suitable treatment regimen for disease
(f) selecting patients for treatment
comprising means for detecting a mutation in the DNA contained Within the sample following treatment with a modifying reagent Further provided are primers and probes useful for the detection of nucleotide alterations and/or the methylation status of a target sequence following treatment with a modifying reagent. The primers and probes disclosed herein may specifically bind to a mutated or non-mutated target sequence or to a methylated or non-methylated target sequence. The primers and probes may be utilized in the presently disclosed methods and kits.

BRIEF DESCRIPTION OF THE DRAWINGS

FIG. 1 illustrates an amplification plot of the wild-type BRAF assay "a" and the mutant BRAF assay "b" for HT29 cell line DNA. (A) Bisulfite converted; (B) Non-bisulfite converted.

FIG. 2 illustrates an amplification plot of the wild-type BRAF assay "a" and the mutant BRAF assay "b" for Colo205 cell line DNA. (A) Bisulfite converted; (B) Non-bisulfite converted.

FIG. 3 illustrates an amplification plot for positive control BRAF DNA (BRAF Therascreen PCR kit, Qiagen). (A) Bisulfite converted; (B) Non-bisulfite converted.

FIG. 6 illustrates an amplification plot for bisulfite converted HCT116 cell line DNA. (A) wild-type KRAS assay "1", KRAS mutant 2.1 assay "2", and KRAS mutant 2.2 assay "3". (B) wild-type KRAS assay "1", KRAS mutant 3.1 assay "2", and KRAS mutant 3.2 assay "3".

FIG. 14 illustrates an amplification plot for non-template control DNA, bisulfite converted. (A) wild-type KRAS assay "1", KRAS mutant 2.1 assay "2", and KRAS mutant 2.2 assay "3". (B) wild-type KRAS assay "1", KRAS mutant 3.1 assay "2", and KRAS mutant 3.2 assay "3".

DETAILED DESCRIPTION OF THE INVENTION

Figure 4:
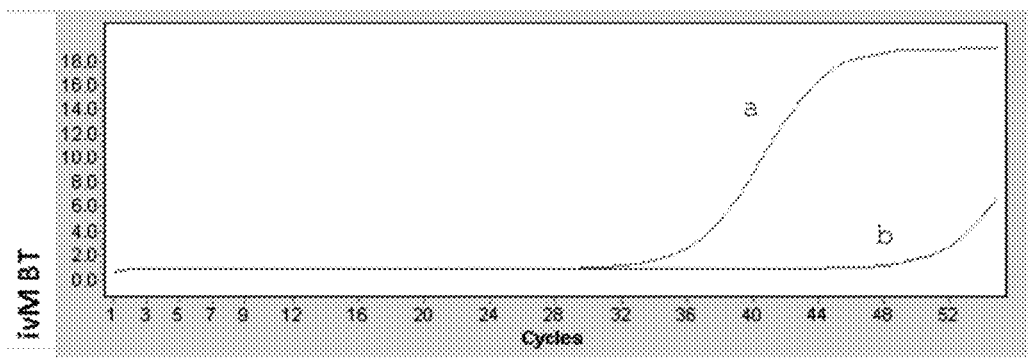
FIG. 4 illustrates an amplification plot for Bisulfite converted DNA. (A) in vitro methylated BRAF DNA; (B) DKO cell line DNA; and (C) Non-template control DNA.
Figure 4:
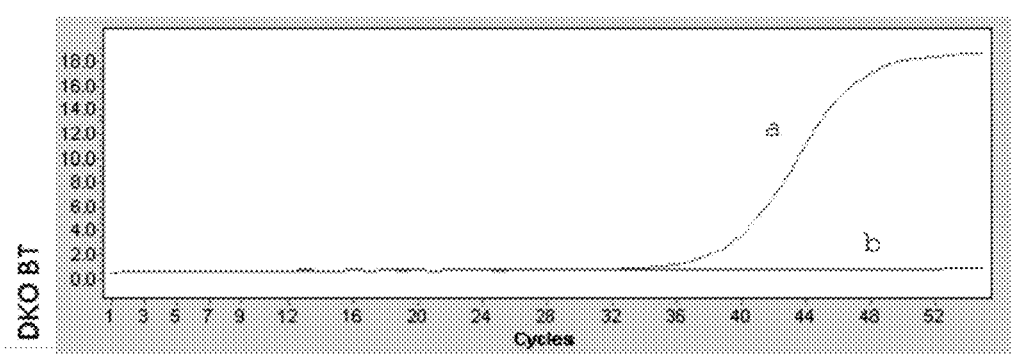
Figure 4:
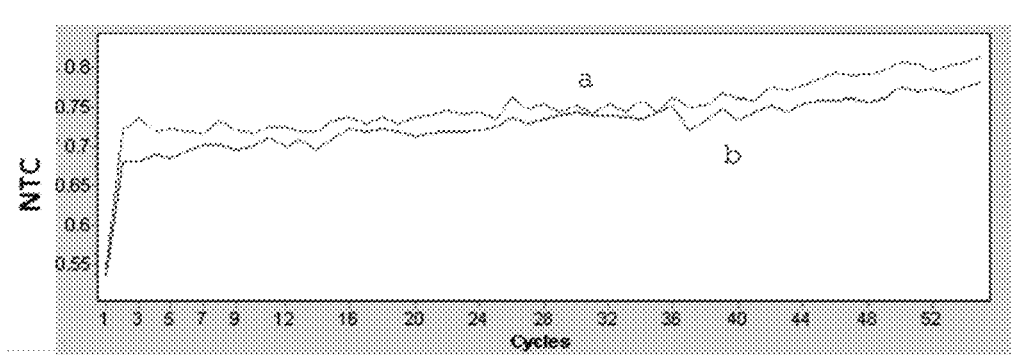

The presently disclosed subject matter may be further described utilizing terms as defined below.

Unless otherwise specified or indicated by context, the terms "a", "an", and "the" mean "one or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus .ltoreq.10% of the particular term and "substantially" and "significantly" will mean plus or minus >10% of the particular term.

As used herein, the terms "include" and "including" have the same meaning as the terms "comprise" and "comprising."

The invention, as set out in the claims, is based upon successful attempts to improve the detection of disease and predictive drug profiling. The invention is based upon a combination of tests for detecting mutation markers and epigenetic modification markers respectively in the same sample, and shown for the first time herein to provide a particularly useful overall test.

The invention provides for a method of detecting the methylation and/or mutation status of particular target sequences, wherein the methylation status (which may be considered aberrant methylation or hypermethylation or hypomethylation or absence of methylation) and/or the mutation status (which may be considered wild type, non-mutated or mutated) of the target sequences is indicative of a predisposition to disease, of the incidence of disease, or useful for predictive drug profiling.

The methods of the invention are preferably ex vivo or in vitro methods carried out on a test sample. The methods are non-invasive. The methods may be used to identify any type of disease.

The "sample" in which to detect the methylation and mutation status of target sequences of interest is a sample comprising nucleic acid molecules. Thus the sample may include cells and/or may include nucleic acid molecules, in particular (genomic) DNA, derived from cells. The sample may thus be a tissue sample, body fluid, body fluid precipitate, cerebrospinal fluid or lavage specimen. Preferably, the test sample is obtained from a human subject. Test samples for diagnostic, prognostic, or personalised medicinal uses can be obtained from surgical samples, such as biopsies or fine needle aspirates, from paraffin embedded tissues, from frozen tumor tissue samples, from fresh tumor tissue samples, from a fresh or frozen body fluid, for example. Non-limiting examples include whole blood, bone marrow, cerebral spinal fluid, peritoneal fluid, pleural fluid, lymph fluid, serum, plasma, urine, chyle, stool, ejaculate, sputum, nipple aspirate, saliva, swabs specimen, wash or lavage fluid and/or brush specimens. The test sample is generally obtained from a (human) subject suspected of being diseased. Alternatively the test sample is obtained from a subject undergoing routine examination and not necessarily being suspected of having a disease. Thus patients at risk can be identified before the disease has a chance to manifest itself in terms of symptoms identifiable in the patient. Alternatively the sample is obtained from a subject undergoing treatment, or from patients being checked for recurrence of disease.

"Detecting" a disease or predisposition to disease is defined herein to include detecting by way of routine examination, screening for a disease or pre-stadia of a disease, monitoring and/or staging the state and/or progression of the disease, checking for recurrence of disease following treatment and monitoring the success of a particular treatment.

The detection can also have prognostic value, and the prognostic value of the tests can be used as a marker of potential susceptibility to disease. Thus patients at risk may be identified before the disease has a chance to manifest itself in terms of symptoms identifiable in the patient. Initial detection as well as follow up detection, for example following treatment, is also included within the definition. Follow up detection may be performed after any treatment. The detection may also link to a disease stage or grade. The "Stage" refers to how far a disease has progressed anatomically, while the "grade" refers to cell appearance (differentiation) and DNA make up.

Preferably the disease is a cancer, a neurodevelopmental disorder such as Rett syndrome, Rubinstein-Taybi syndrome, Coffi n-Lowry syndrome, ATRX syndrome, a neurodegenerative disorder such as Alzheimer's disease, Parkinson's disease, Huntington's disease, a neurological disease such as Multiple sclerosis, Amyotrophic lateral sclerosis, Epilepsy, or a cardiovascular disease. "Cancer" refers to the presence of cells possessing characteristics typical of cancer-causing cells, such as uncontrolled proliferation, immortality, metastatic potential, rapid growth and proliferation rate, and certain characteristic morphological features.

The term "methylation status" refers to the presence or absence of a methylated cytosine residue in one or more CpG dinucleotides within the nucleic acid or gene of interest. In many genes, the CpG islands are found in the promoter region and may begin (just) upstream of a promoter and extend downstream into the transcribed region. Methylation of a CpG island at a promoter often prevents expression of the gene. The islands can also surround the 5' region of the coding region of the gene as well as the 3' region of the coding region. Thus, CpG islands can be found in multiple regions of a nucleic acid sequence including upstream of coding sequences in a regulatory region including a promoter region, in the coding regions (e.g. exons), downstream of coding regions in, for example, enhancer regions, and in introns. All of these regions can be assessed to determine their methylation status, as appropriate. In certain embodiments, the methylation status of the gene is assessed by determining levels of methylation in the promoter, intron, exon1 and/or exon2 region of the gene. A "promoter" is a region upstream from the transcription start site (TSS), extending between approximately 10 Kb, 4 Kb, 3 Kb, 1 Kb, 500 bp or 150 to 300 bp from the TSS. When the CpG distribution in the promoter region is rather scarce, levels of methylation may be assessed in the intron and/or exon regions. The region for assessment may be a region that comprises both intron and exon sequences and thus overlaps both regions. CpG islands are readily identifiable through a range of techniques, including sequencing and in silico predictive methods.

"Mutation" refers to any change in the sequence of nucleic acid or gene of interest. There are many different types of mutation. They can occur on a macroscopic level in the form of chromosomal mutations, gene rearrangements or they may be the result of a single base pair change in the sequence. Mutations can occur within a gene preventing the synthesis of the correct protein, they may occur in gene promoter regions or in DNA regulatory regions changing the expression levels of the protein, or near the splice sites in introns causing disruption to the splicing process and production of an incorrect protein. Heterogeneity of mutation may occur and indicate the presence of a mutated form as well as a wild type form. Typically, individuals for which heterogeneity is observed are indicated to be carrier of the mutation. Alternatively, the heterogeneity may involve mutated forms only and in such case more than one mutation may be detected.

In the present invention, oligonucleotides that hybridize specifically to a mutated or non-mutated target sequence or that hybridize specifically to a modified non-methylated target sequence or methylated target sequence may be utilized as primers or probes for detecting the mutated or non-mutated target sequence or the modified non-methylated target sequence or methylated target sequence. "Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to about 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Equations for calculating Tm and conditions for nucleic acid hybridization are known in the art.

"Primer" refers to an oligonucleotide that is capable of acting as a point of initiation of synthesis when placed under conditions in which primer extension is initiated (e.g., primer extension associated with an application such as PCR). An oligonucleotide "primer" may occur naturally, as in a purified restriction digest or may be produced synthetically. Primers contemplated herein may include, but are not limited to, oligonucleotides that comprise the nucleocleotide sequence of any of SEQ ID NOs:1-16.

A "probe" refers to an oligonucleotide that interacts with a target nucleic acid via hybridization. A probe may be fully complementary to a target nucleic acid sequence or partially complementary. The level of complementarity will depend on many factors based, in general, on the function of the probe. A probe or probes can be used, for example to detect the presence or absence of a mutation in a nucleic acid sequence by virtue of the sequence characteristics of the target. Probes can be labeled or non-labeled, or modified in any of a number of ways well known in the art. A probe may specifically hybridize to a target nucleic acid.

A "target nucleic acid" refers to a nucleic acid molecule containing a sequence that has at least partial complementarity with a probe oligonucleotide and/or a primer oligonucleotide. A primer or probe may specifically hybridize to a target nucleic acid. Target nucleic acid may refer to nucleic acid of the KRAS gene and/or the BRAF gene.

The term "amplification" or "amplifying" refers to the production of additional copies of a nucleic acid sequence. Amplification is generally carried out using polymerase chain reaction (PCR) technologies known in the art. The term "amplification reaction system" refers to any in vitro means for multiplying the copies of a target sequence of nucleic acid. The term "amplification reaction mixture" refers to ah aqueous solution comprising the various reagents used to amplify a target nucleic acid. These may include enzymes (e.g., a thermostable polymerase), aqueous buffers, salts, amplification primers, target nucleic acid, and nucleoside triphosphates, and optionally at least one labeled probe and/or optionally at least one agent for determining the melting temperature of an amplified target nucleic acid (e.g., a fluorescent intercalating agent that exhibits a change in fluorescence in the presence of double-stranded nucleic acid).

As used herein the term "sequencing" as in determining the sequence of a polynucleotide refers to methods that determine the base identity at multiple base positions or determine the base identity at a single position. "Detecting nucleic acid" as contemplated herein, may include "sequencing nucleic acid."

In the present invention, the presence and/or amount of a mutated or non-mutated first target sequence and eventually of a methylated or non-methylated second target sequence in a sample of interest is assessed, in all embodiments, the presence and/or amount of mutation may be detected in one, two, three, four, five of more target sequences. Likewise, the presence and/or amount of methylation may be detected in one, two, three, four, five of more target sequences. Target sequences may apply to a same region or gene, or alternatively to different regions or genes in the DNA. Accordingly, the first target sequence and the second target sequence as used herein, may apply to the same gene. Alternatively, first target sequence and second target sequence may apply to different genes. In preferred embodiments, the target sequence applies to genes involved in the EGFR signalling pathway, including KRAS and BRAF. The identification of the role of EGFR signalling pathway in cancer has led to the development of anti-cancer therapeutics directed against the EGFR protein, including Gefitinib (Iressa®, AstraZeneca) and Erlotinib (Tarceva®, Roche) for non-small-cell lung cancer, and Panitumumab (Vectibix®, Amgen) and Cetuximab (Erbitux®, Merck Serono) for colorectal cancer. The first two are small compound inhibitors of the intracellular tyrosine kinase region of EGFR, whereas the latter two are antibody proteins that block the extracellular region of EGFR. The KRAS gene encodes the KRAS protein which stimulates signaling pathways downstream from EGFR. KRAS mutations lead to a constitutively activated, mutated KRAS protein that continually stimulates these downstream pathways. Such KRAS gene mutations are often found in e.g. colorectal, pancreatic and lung cancer tumours. Although EGFR tyrosine kinase inhibitors (TKIs) can block EGFR activation, they cannot block the activity of the mutated KRAS protein. Thus, patients with KRAS mutations tend to be resistant to erlotinib and gefitinib.[2,5-7] BRAF is another important protein involved in the EGFR signalling pathway where it acts downstream from KRAS. Mutated BRAF gene is associated with poor prognosis and poor response to anti-EGFR therapeutics in colorectal cancer. In certain embodiments, BRAF mutation testing may be combined with KRAS mutation testing. In certain embodiments, the methylation status of particular target sequences in the pTEN or p16 gene is detected, with detection of a methylation in pTEN or p16 providing an indication of a predisposition to, or incidence of, cancer.

In preferred embodiments, the methylation status is detected in particular target sequences of at least one gene selected from BRAF-KRAS and the mutation status is detected in particular target sequences of at least one gene selected from pTEN and p16, with detection of the methylation modification in at least one of the genes and the mutation in at least one of the genes providing an indication of a predisposition to, or incidence of, cancer, or being indicative for response to treatment with a particular drug.

As shown herein, the methylation marker assay and mutation test give very specific and sensitive results.

KRAS is the gene symbol approved by the HUGO Gene Nomenclature Committee. The gene is located on chromosome 12 (location 12p12.1) and the gene sequence is listed under the accession number NC_000012.11. The gene encodes the v-Ki-ras2 Kirsten rat sarcoma viral oncogene homolog. The corresponding mRNA's and proteins are listed under NM_004985.3, NM_033360.2, NP_004976.2 and NP_203524.1.

BRAF is the gene symbol approved by the HUGO Gene Nomenclature Committee. The gene is located on chromosome 7 (location 7q34) and the gene sequence is listed under the accession number NC_000007.13. The gene encodes the v-raf murine sarcoma viral oncogene homolog b1. The corresponding mRNA and protein is listed under NM_004333.4 and NP_004324.2

CDKN2A is the gene symbol approved by the HUGO Gene Nomenclature Committee for p16. The gene is located on chromosome 9 (location 9p21) and the gene sequence is listed under the accession numbers NC_000009.11. The gene encodes the cyclin-dependent kinase inhibitor 2A. the corresponding mRNA's and proteins are listed under NM_000077.4, NM_001195132.1, NM_058197.4. NM_058195.3 and NP_000068.1, NP_001182061.1, NP_478104.2 and NP_478102.2

PTEN is the gene symbol approved by the HUGO Gene Nomenclature Committee. The gene is located on chromosome 10 (location 10Q23:3) and the gene sequence is listed under the accession number NC000010.10. The gene encodes the phosphatase and tensin homolog. The corresponding mRNA and protein is listed under NM_000314.4, and NP_000305.3

By "gene" is meant the specific known gene in question. It may also relate to any gene which is taken from the family to which the named "gene" belongs, in certain circumstances, and includes according to all aspects of the invention not only the particular sequences found in the publicly available database entries, but also encompasses transcript and nucleotide variants of these sequences, with the proviso that methylation or another epigenetic modification of the gene is linked to the incidence of colorectal cancer. Variant sequences may have at least 90%, at least 91%, at least 92%, at least 93%, at least 94%, at least 95%, at least 96%, at least 97%, at least 98%, or at least 99% nucleotide sequence identity with the nucleotide sequences in the database entries. Computer programs for determining percentage nucleotide sequence identity are available in the art, including the Basic Local Alignment Search Tool (BLAST) available from the National Center for Biotechnology information.

As shown in the example section, the invention provides for methylation-dependent modification of the nucleic acid in a sample, and subsequently uses nucleic acid amplification processes to distinguish between mutated and non-mutated target sequence, in contrast to previous methods, the presence of a mutated or non-mutated target sequence is detected in a converted nucleic acid, allowing combined mutation and methylation detection in the same sample. Suitable techniques for assessing the mutation status of target sequences are polymerase chain reaction and sequencing.

Approaches for detecting methylated CpG dinucleotide motifs may use chemical reagents that selectively modify either the methylated or non-methylated form of CpG dinucleotide motifs. Suitable modifying reagents include hydrazine and bisulphite ions. In certain embodiments, the methods of the invention may use bisulphite ions. Bisulfite attaches itself to the C-6 of the cytosine ring. Subsequently, under alkaline conditions, the sulfonated cytosine is deaminated and desulfonated to uracil. The presence of a methyl group at the C-5 position prevents sulfonation and, therefore, methylcytosine remains the same. When PCR is performed on the bisulfite-treated DNA, uracil (from cytosine) results in thymine and methylcytosine in cytosine (Furuichi et al., 1970). It is general knowledge that the resulting uracil has the base pairing behaviour of thymidine which differs from cytosine base pairing behaviour. This makes the discrimination between methylated and non-methylated cytosines possible. Useful conventional techniques of molecular biology and nucleic acid chemistry for assessing sequence differences are well known in the art and explained in the literature. See, for example, Sambrook, J., et al., Molecular cloning: A laboratory Manual, (2001) 3rd edition, Cold Spring Harbor, N.Y.; Gait, M. J. (ed.), Oligonucleotide Synthesis, A Practical Approach, IRL Press (1984); Hames B. D., and Higgins, S. J. (eds.). Nucleic Acid Hybridization, A Practical Approach, IRL Press (1985); and the series, Methods in Enzymology, Academic Press, Inc.

In a preferred embodiment, assessment of the methylation and/or mutation status of the relevant nucleic acid target requires amplification to yield amplification products. The presence of amplification products may be assessed directly using methods well known in the art. They simply may be visualized on a suitable gel, such as an agarose or polyacrylamide gel. Detection may involve the binding of specific dyes, such as ethidium bromide, which intercalate into double-stranded DNA and visualisation of the DNA bands under a UV illuminator for example. Another means for detecting amplification products comprises hybridization with oligonucleotide probes. Alternatively, fluorescence or energy transfer can be measured to determine the presence of the methylated DNA.

Some techniques use primers for assessing the mutation status and/or the methylation status at CpG dinucleotides. Two approaches to primer design are possible. Firstly, primers may be designed that themselves do not cover any potential sites of mutation and/or DNA methylation. Sequence variations at sites of mutation and/or differential methylation are located between the two primers and visualisation of the sequence variation requires further assay steps. Examples of techniques using such methylation primers are bisulphite genomic sequencing, COBRA, Ms-SnuPE and several other techniques. Secondly, primers may be designed that hybridize specifically with either the methylated or non-methylated version and/or with the mutated or non-mutated version of the initial treated sequence.

Because the two strands of DNA are no longer complementary after bisulfite modification, strand-specific primers are used when PCR amplification is applied. Either the sense strand or antisense strand can be chosen for primer design. Primers are designed under the assumption that all cytosines had been converted to uracil. In practice, in a known DNA sequence, all non-CPG cytosines are converted to uracil resulting in a converted DNA sequence The first primer is designed to base-pair with this converted sequence (normally this would be thought of as the reverse primer). The second (forward) primer is designed to base-pair to the extension of the first primer and not the "opposite strand" like in traditional PCR. After primer hybridization, an amplification reaction can be performed and amplification products assayed using any detection system known in the art. The presence of an amplification product indicates that a sample hybridized to the primer. The specificity of the primer indicates whether the DNA had been modified or not, which in turn indicates whether the DNA had been methylated, mutated or not. If there is a sufficient region of complementarity, e.g., 12, 15, 18, or 20 nucleotides, to the target, then the primer may also contain additional nucleotide residues that do hot interfere with hybridization but may be useful for other manipulations. Examples of such other residues may be sites for restriction endonuclease cleavage, for ligand binding or for factor binding or linkers or repeats. The oligonucleotide primers may or may not be such that they are specific for modified methylated residues.

A further way to distinguish between modified and unmodified nucleic acid is to use oligonucleotide probes. Such probes may hybridize directly to modified nucleic acid or to further products of modified nucleic acid, such as products obtained by amplification. Probe-based assays exploit the oligonucleotide hybridisation to specific sequences and subsequent detection of the hybrid. There may also be further purification steps before the amplification product is detected e.g. a precipitation step. Oligonucleotide probes may be labelled using any detection system known in the art. These include but are not limited to fluorescent moieties, radioisotope labelled moieties, bioluminescent moieties, luminescent moieties, chemiluminescent moieties, enzymes, substrates, receptors, or ligands.

PCR amplification may involve use of hairpin primers (Amplifluor); hairpin probes (Molecular Beacons), hydrolytic probes (Taqman), FRET probe pairs (Lightcycler), primers incorporating a hairpin probe (Scorpion), fluorescent dyes (SYBR Green etc.), primers incorporating the complementary sequence of a DNAzyme and a cleavable fluorescent DNAzyme substrate or oligonucleotide blockers, for example. The methods may apply suitable primers (forward and reverse primers) comprising, consisting essentially of or consisting of the nucleotide sequences set forth in the Table 1 below

TABLE 1

Assay details

| Name assay | Sequence forward | Sequence reverse |
|---|---|---|
| BRAF Wild-type1 | CTTCATAAAAACCTCACAATA AAAATAAATAATTTTAATCTA ACTACAAT (SEQ ID NO. 1) | AGTAGTATTTTAGGGTTAAAA ATTTAATTAGTGGAAAAATAG (SEQ ID NO. 2) |
| BRAF Mutant 1 | CTTCATAAAAACCTCACAATA AAAATAAATAATTTTAATCTA ACTACAAA (SEQ ID NO. 3) | AGTAGTATTTTAGGGTTAAAA ATTTAATTAGTGGAAAAATAG (SEQ ID NO. 2) |
| KRAS Wild-type 1 | TTTGTTGAAAATGATTGAATA TAAATTTGTGGTAGTTGGAGT TG (SEQ ID NO. 4) | CCTACACCAATAATATACATA TTAAAACAAAATTTACCTC (SEQ ID NO. 12) |
| KRAS Mutant 1 | TTTGTTGAAAATGATTGAATA TAAATTTGTGGTAGTTGGAGT TA (SEQ ID NO. 5) | CCTACACCAATAATATACATA TTAAAACAAAATTTACCTC (SEQ ID NO. 12) |
| KRAS Wild-type 2 | GAAAATGATTGAATATAAATT TGTGGTAGTTGGAGTTGGTGG (SEQ ID NO. 6) | CCTACACCAATAATATACATA TTAAAACAAAATTTACCTC (SEQ ID NO. 12) |
| KRAS Mutant 2.1 | GAAAATGATTGAATATAAATT TGTGGTAGTTGGAGTTGGTGT (SEQ ID NO. 7) | CCTACACCAATAATATACATA TTAAAACAAAATTTACCTC (SEQ ID NO. 12) |
| KRAS Mutant 2.2 | GAAAATGATTGAATATAAATT TGTGGTAGTTGGAGTTGGTGA (SEQ ID NO. 8) | CCTACACCAATAATATACATA TTAAAACAAAATTTACCTC (SEQ ID NO. 12) |

TABLE 1-continued

Assay details

| Name assay | Sequence forward | Sequence reverse |
|---|---|---|
| KRAS Wild-type 3 | TTTGTTGAAAATGATTGAATA TAAATTTGTGGTAGTTGGAGT TGG (SEQ ID NO. 9) | CCTACACCAATAATATACATA TTAAAACAAAATTTACCTC (SEQ ID NO. 12) |
| KRAS Mutant 3.1 | TTTGTTGAAAATGATTGAATA TAAATTTGTGGTAGTTGGAGT TGA (SEQ ID NO. 10) | CCTACACCAATAATATACATA TTAAAACAAAATTTACCTC (SEQ ID NO. 12) |
| KRAS Mutant 3.2 | TTTGTTGAAAATGATTGAATA TAAATTTGTGGTAGTTGGAGT TGT (SEQ ID NO. 11) | CCTACACCAATAATATACATA TTAAAACAAAATTTACCTC (SEQ ID NO. 12) |
| P16_7_14 | TTAGGTAAGGGACGTCG (SEQ ID NO. 13) | ACCACATTCGCTAAATACTCG (SEQ ID NO. 14) |
| ACTB | TAGGGAGTATATAGGTTGGGG AAGTT (SEQ ID NO. 15) | AACACACAATAACAAACACAA ATTCAC (SEQ ID NO. 16) |

Multiplex-PCR uses several pairs of primers annealing to different target sequences. This permits the simultaneous analysis of multiple targets in a single sample. For example, in testing for genetic mutations, 2, 3, 4, 5 or more amplifications might be combined. In testing for genetic mutations and assessing methylation status simultaneously, first target sequence and second target sequence may apply to the same gene. Alternatively, first target sequence and second target sequence may apply to different genes.

In the MSP approach, DNA may be amplified using primer pairs designed to distinguish methylated from non-methylated DNA by taking advantage of sequence differences as a result of sodium-bisulphite treatment (Herman et al., 1996; and WO 97/46705). For example, bisulphite ions modify non-methylated cytosine bases, changing them to uracil bases. Uracil bases hybridize to adenine bases under hybridization conditions. Thus an oligonucleotide primer which comprises adenine bases in place of guanine bases would hybridize to the bisulphite-modified DNA, whereas an oligonucleotide primer containing the guanine bases would hybridize to the non-modified (methylated) cytosine residues in the DNA. Amplification using a DNA polymerase and a second primer yield amplification products which can be readily observed, which in turn indicates whether the DNA had been methylated or not. Whereas PCR is a preferred amplification method, variants on this basic technique such as nested PCR and multiplex PCR are also included within the scope of the invention.

A specific example of the MSP technique is designated: real-time quantitative MSP (QMSP), and permits reliable quantification of methylated DNA in real time or at end point. Real-time methods are generally based on the continuous optical monitoring of an amplification procedure and utilise fluorescently labelled reagents whose incorporation in a product can be quantified and whose quantification is indicative of copy number of that sequence in the template. One such reagent is a fluorescent dye, called SYBR Green I that preferentially binds double-stranded DNA and whose fluorescence is greatly enhanced by binding of double-stranded DNA. Alternatively, labelled primers and/or labelled probes can be used for quantification. They represent a specific application of the well-known and commercially available real-time amplification techniques such as TAQMAN®, MOLECULAR BEACONS®, AMPLIFLUOR® and SCORPION®, DzyNA®, Plexor™ etc. in the real-time PCR systems, it is possible to monitor the PCR reaction during the exponential phase where the first significant increase in the amount of PCR product correlates to the initial amount of target template.

Real-Time PCR detects the accumulation of amplicon during the reaction. Real-time methods do not need to be utilised, however. Many applications do not require quantification and Real-Time PCR is used only as a tool to obtain convenient results presentation and storage, and at the same time to avoid post-PCR handling. Thus, analyses can be performed only to confirm whether the target DNA is present in the sample or not. Such end-point verification is carried out after the amplification reaction has finished. This knowledge can be used in a medical diagnostic laboratory to detect a predisposition to, or the incidence of, cancer in a patient. End-point PCR fluorescence detection techniques may employ the same approaches as widely used for Real Time PCR. For example, instruments such as "Gene" detector ("Gene-Machine") allow the measurement of fluorescence directly in PCR tubes (available from Bioron, see http://www.bioron.net/excellent-products-from-bioron/fluorescent-detector.html).

In real-time embodiments, quantitation may be on an absolute basis, or may be relative to a constitutively methylated DNA standard, or may be relative to a non-methylated DNA standard. Methylation status may be determined by using the ratio between the signal of the marker under investigation and the signal of a reference gene where methylation status is known (such as β-actin (=ActB) for example), or by using the ratio between the methylated marker and the sum of the methylated and the non-methylated marker. Alternatively, absolute copy number of the methylated marker gene can be determined.

Suitable controls may need to be incorporated in order to ensure the method chosen is working correctly and reliably. Suitable controls may include assessing the methylation status of a gene known to be methylated. This experiment acts as a positive control to help to ensure that false negative results are not obtained. The gene may be one which is known to be methylated in the sample under investigation or it may have been artificially methylated, for example by using a suitable methyltransferase enzyme, such as SssI methyltransferase.

Additionally or alternatively, suitable negative controls may be employed with the methods of the invention. Here, suitable controls may include assessing the methylation status of a gene known to be non-methylated or a gene that has been artificially demethylated. This experiment acts as a negative control to ensure that false positive results are not obtained. In one embodiment, the gene selected from KRAS and BRAF may be assessed in normal cells as a negative control.

Sequencing methods such as Sanger sequencing, pyrosequencing, bridge amplification sequencing, TAS, etc., may be used for assaying the methylation and/or mutation status of a target sequence. Other applicable methods for DNA sequencing include microelectrophoretic methods (Blazej, R. G., et al., 2006 Proc. Natl. Acad. Sci. USA 103, 7240-7245), sequencing by hybridization (Gresham, D. et al., 2008 Nat. Rev. Genet. 9, 291-302), real-time sequencing (Soni, G. V. et al., 2007. Clin. Chem. 53, 1996-2001 (2007) Healy, K. 2007 Nanomed. 2, 459-481) and cyclic-array sequencing Shendure, J. et al 2005 Science 309, 1728-1732. Margulies, M. et al, 2005 Nature 437, 376-380). In microelectrophoretic methods, conventional electrophoretic sequencing is carried out on a microfabricated device resulting in faster processing times and substantial reduction in reagent consumption. In sequencing by hybridization, variant positions of target sequences are identified by differential hybridization of labeled nucleic acid fragments to an array of oligonucleotide probes. Pyrosequencing is a sequencing method based on the "sequencing by synthesis" principle. "Sequencing by synthesis" involves taking a single strand of the DNA to be sequenced and then synthesizing its complementary strand enzymatically. Essentially, the method allows sequencing of a single strand of DNA by synthesizing the complementary strand along it, one base pair at a time, and detecting which base was actually added at each step. It differs from Sanger sequencing, in that it relies on the detection of pyrophosphate release on nucleotide incorporation, rather than chain termination with dideoxynucleotides. The 454 Sequencing uses a large-scale parallel pyrosequencing system that relies on fixing nebulized and adapter-ligated DNA fragments to small DNA-capture beads in a water-in-oil emulsion. The DNA fixed to these beads is then amplified by PCR.

Due to the fact that bisulfite treatment of non-methylated cytosine results in thymine, discrimination of a mutation "cytosine to thymine" following DNA conversion of a sequence may not be possible. In such case, assessment of the converted opposite strand sequence will indicate whether a mutation was all or not present. An adenine on the opposite strand would indicate the presence of a "cytosine to thymine" mutation. Thus, combined methylation and mutation status assessment may involve investigation of both bisulfite treated DNA strands.

The methods and assays of the present invention are not only useful for diagnosis but also useful for selecting patients (suitable) for treatment, for predicting the likelihood of successful treatment of a patient and can be used to aid patient therapy selection. In related aspects, the invention provides:

A method for predicting the likelihood of successful treatment of cancer comprising detecting the presence and/or amount of a mutated or non-mutated target sequence of interest in a DNA-containing sample following treatment with a modifying reagent, wherein the detection of the mutation is indicative that the likelihood of successful treatment is lower than if the mutation is not detected.

A method for predicting the likelihood of resistance to treatment of cancer of comprising detecting the presence and/or amount of a mutated or non-mutated target sequence of interest in a DNA-containing sample following treatment with a modifying reagent, wherein the detection of the mutation is indicative that the likelihood of resistance to treatment is higher than if the mutation is not detected.

A method of selecting a suitable treatment regimen for cancer comprising detecting the presence and/or amount of a mutated or non-mutated target sequence of interest in a DNA-containing sample following treatment with a modifying reagent.

The invention also relates to a kit for detecting a predisposition to, or the incidence of, disease in a sample comprising means for detecting a mutation in the DNA contained within the sample following treatment with a modifying reagent, wherein detection of the mutation is indicative of a predisposition to, or the incidence of, disease.

A kit for detecting the presence and/or amount of a mutated or non-mutated first target sequence and of a methylated or non-methylated second target sequence in a sample of interest comprising:
(a) Means for detecting a mutation in the DNA contained within the sample following treatment with a modifying reagent, wherein detection of the mutations is indicative of disease or predisposition to disease, or is indicative for response to a particular treatment with a drug or therapy. and
(b) means for detecting the presence of methylation in the DNA contained within the sample following treatment with a modifying reagent, wherein detection of the methylation is indicative of disease, or predisposition to disease, or is indicative for response to a particular treatment with a drug or therapy.

The invention also relates to a kit for detecting a predisposition to, or the incidence of, disease in a sample comprising:
(a) means for detecting an epigenetic modification in the DNA contained within the sample following treatment with a modifying reagent, wherein detection of the epigenetic modification is indicative of a predisposition to, or the incidence of, disease, and
(b) means for detecting a mutation in the DNA contained within the sample following treatment with a modifying reagent, wherein detection of the mutation is indicative of a predisposition to, or the incidence of, disease.

Also provided is a kit for any of:
(a) detecting a predisposition to, or the incidence of, disease in a sample
(b) monitoring treatment of disease
(c) predicting the likelihood of successful treatment of disease
(d) predicting the likelihood of resistance to treatment of disease
(e) selecting a suitable treatment regimen for disease comprising means for detecting a mutation in the DNA contained within the sample following treatment with a modifying reagent in a panel of at least two genes.

Further provided are primers and probes useful for the detection of nucleotide alterations and/or methylation status of a target sequence following treatment with a modifying reagent. The primers and probes disclosed herein may specifically bind to a mutated or non-mutated target sequence or to a methylated or non-methylated target sequence The primers and probes may be utilized in the presently disclosed methods and kits.

EXPERIMENTAL SECTION

Example 1

Samples

Four cell lines, SW620, HCT116, HT29 and Colo205 were investigated for the presence of mutations as indicated in table 2.

TABLE 2

Cell lines used for the detection of mutations.

| Cell line | Gene | Mutation |
|---|---|---|
| SW620 | KRAS | G12V |
| HCT116 | KRAS | G13D |
| HT29 | BRAF | V600E |
| Colo205 | BRAF | V600E |

DNA Modification

The genomic DNA from the cell lines (table 1) was treated using the EZ DNA Methylation Kit from Zymo Research according to the manufacturer's protocol. One ug of genomic DNA for every cell line was converted into BT-DNA in a volume of 50 ul by use of 100 ul of CT Conversion Reagent at 70° C. for 3 hours. Following this incubation, the samples were bound to the supplied columns and 200 ul of desulfonation buffer was added. Desulfonation was carried out at room temperature for 20 minutes. The columns were washed twice and the modified DNA was eluted into 50 ul elution buffer, which results into a final concentration of 20 ng/ul. After the treatment the samples are stored at −80° C. for further analysis.

Mutation Detection

TABLE 3

Mutation details for BRAF

| Mutation | Base change | Cosmic ID |
|---|---|---|
| V600E | 1799T > A | 476 |

TABLE 4

Mutations details for KRAS:

| Mutation | Base change | Cosmic ID |
|---|---|---|
| GLY12Ser | (GGT > AGT) | 517 |
| GLY12Val | (GGT > GTT) | 520 |
| GLY13Asp | (GGC > GAC) | 532 |

Primer Sequences

TABLE 5

Designed primers for BRAF

| Name | Sequence forward | Sequence reverse |
|---|---|---|
| BRAF Wild-type1 | CTTCATAAAAACCTCACAATA AAAATAAATAATTTTAATCTA ACTACAAT (SEQ ID NO. 1) | AGTAGTATTTTAGGGTTAAAA ATTTAATTAGTGGAAAAATAG (SEQ ID NO. 2) |
| BRAF Mutant 1 | CTTCATAAAAACCTCACAATA AAAATAAATAATTTTAATCTA ACTACAAA (SEQ ID NO. 3) | AGTAGTATTTTAGGGTTAAAA ATTTAATTAGTGGAAAAATAG (SEQ ID NO. 2) |

TABLE 6

Designed primers for KRAS

| Name | Sequence forward | Sequence reverse |
|---|---|---|
| KRAS Wild-type 1 | TTTGTTGAAAATGATTGAATA TAAATTTGTGGTAGTTGGAGT TG (SEQ ID NO. 4) | CCTACACCAATAATATACATA TAAAACAAAATTACCTC (SEQ ID NO. 12) |
| KRAS Mutant 1 | TTTGTTGAAAATGATTGAATA TAAATTTGTGGTAGTTGGAGT TA (SEQ ID NO. 5) | CCTACACCAATAATATACATA TAAAACAAAATTACCTC (SEQ ID NO. 12) |
| KRAS Wild-type 2 | GAAAATGATTGAATATAAATT TGTGGTAGTTGGAGTTGGTGG (SEQ ID NO. 6) | CCTACACCAATAATATACATA TAAAACAAAATTACCTC (SEQ ID NO. 12) |
| KRAS Mutant 2.1 | GAAAATGATTGAATATAAATT TGTGGTAGTTGGAGTTGGTGT (SEQ ID NO. 7) | CCTACACCAATAATATACATA TAAAACAAAATTACCTC (SEQ ID NO. 12) |
| KRAS Mutant 2.2 | GAAAATGATTGAATATAAATT TGTGGTAGTTGGAGTTGGTGA (SEQ ID NO. 8) | CCTACACCAATAATATACATA TAAAACAAAATTACCTC (SEQ ID NO. 12) |
| KRAS Wild-type 3 | TTTGTTGAAAATGATTGAATA TAAATTTGTGGTAGTTGGAGT TGG (SEQ ID NO. 9) | CCTACACCAATAATATACATA TAAAACAAAATTACCTC (SEQ ID NO. 12) |
| KRAS Mutant 3.1 | TTTGTTGAAAATGATTGAATA TAAATTTGTGGTAGTTGGAGT TGA (SEQ ID NO. 10) | CCTACACCAATAATATACATA TAAAACAAAATTACCTC (SEQ ID NO. 12) |
| KRAS Mutant 3.2 | TTTGTTGAAAATGATTGAATA TAAATTTGTGGTAGTTGGAGT TGT (SEQ ID NO. 11) | CCTACACCAATAATATACATA TAAAACAAAATTACCTC (SEQ ID NO. 12) |

Expected result: For BRAF V600E, both HT29 and Colo205 should be positive.

Results for BRAF

In this experiment, the BRAF primers designed for detecting the wild-type genomes and BRAF primers designed for detecting the mutation V600E were tested on the cell lines HT29 and COLO205 (both bisulfite treated and non-treated), on in vitro methylated DNA and on DKO, by use of the Roche SYBR green mix. Both DKO and in vitro methylated DNA were bisulfite converted FIGS. 1-4 show the amplification plots of the wild-type BRAF assay indicated by "a" and the mutant BRAF assay indicated by "b", as performed on the following samples:

HT29 cell line bisulfite converted DNA

HT29 cell line non-bisulfite converted DNA

Colo205 cell line bisulfite converted DNA

Colo205 cell line non-bisulfite converted DNA

Positive control bisulfite converted (BRAF Therascreen PCR kit, Qiagen)

Non-bisulfite Positive control non Bisulfite converted

In vitro methylated (ivM) DNA bisulfite converted BRAF DNA

DKO cell line bisulfite converted DNA

Non template control (NTC) DNA

Caliper LC90 Results

After PCR reactions all reactions were toad on the LC90, an electrophoresis system to confirm presence or absence of a specific product.

Figure 5:
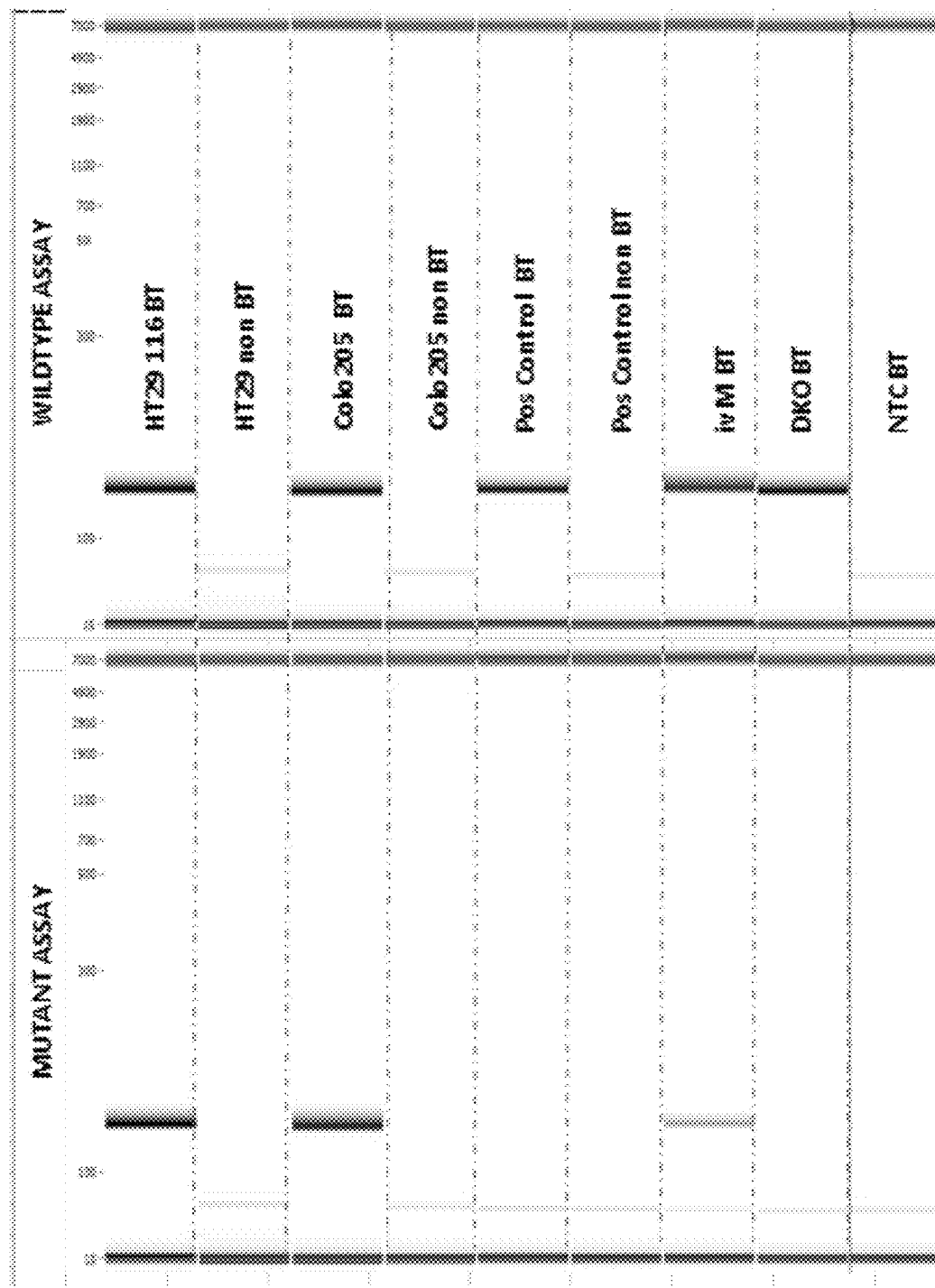
FIG. 5 illustrates gel electrophoresis separation of the amplified products for FIGS. 1-4.

Conclusion:

The designed BRAF MUT-PRIMERS are specific for bisulfite converted DNA since no amplification is observed for non-bisulfite converted HT29 or for COLO205 DNA (FIG. 5 lane 2 and lane 4). Amplification on HT29 bisulfite converted DNA and COLO205 bisulfite converted DNA, both for wild-type and mutated assay was observed (FIG. 5 lane 1 and lane 3). Both cell lines are described as carriers of the mutation. Probably there is heterogeneity of the mutation in the HT29 and COLO205 cell lines. Amplification was observed with the wild-type assay on ivM, and also amplification was observed with the mutation assay on ivM, but it comes up very late (Ct>45). Only amplification of wild-type assay in DKO was observed.

Results for KRAS

In this experiment the KRAS primers for detecting the wild-type genomes and KRAS primers for detecting the mutations were tested on HCT116, SW620 (both bisulfite treated and non-treated), in vitro methylated DNA and on DKO, by use of the Roche SYBR green mix.

Both DKO and in vitro methylated DNA were Bisulfite converted.

Figure 7:
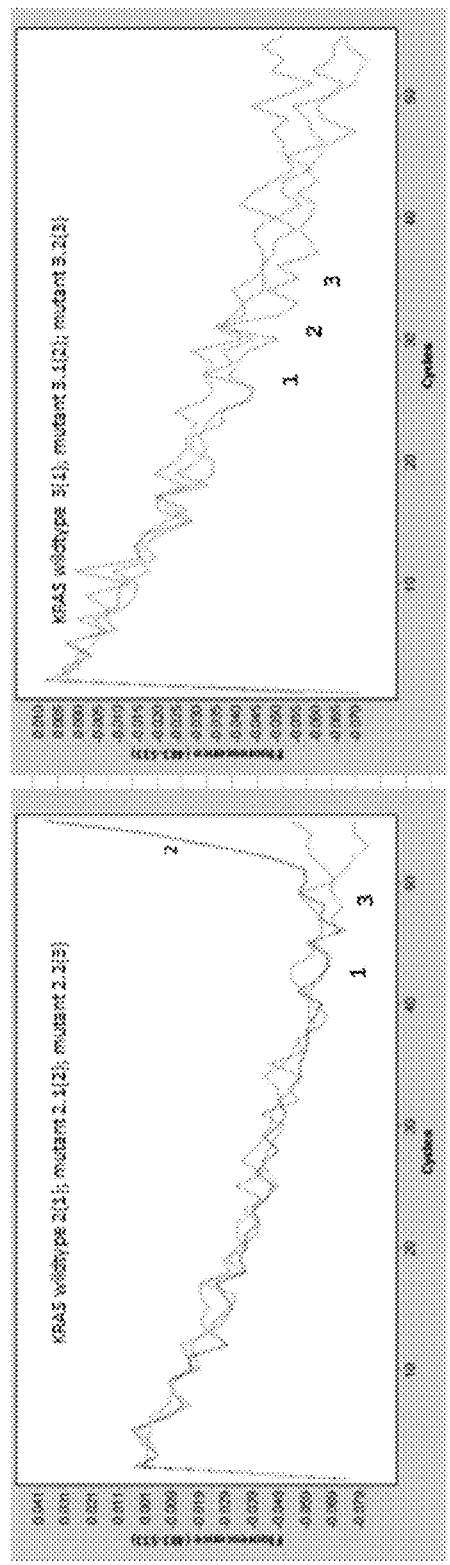
FIG. 7 illustrates ah amplification plot for non-bisulfite converted HCT116 cell line DNA. (A) Wild-type KRAS assay "1", KRAS mutant 2.1 assay "2", and KRAS mutant 2.2 assay "3". (B) wild-type KRAS assay "1", KRAS mutant 3.1 assay "2", and KRAS mutant 3.2 assay "3".
Figure 8:
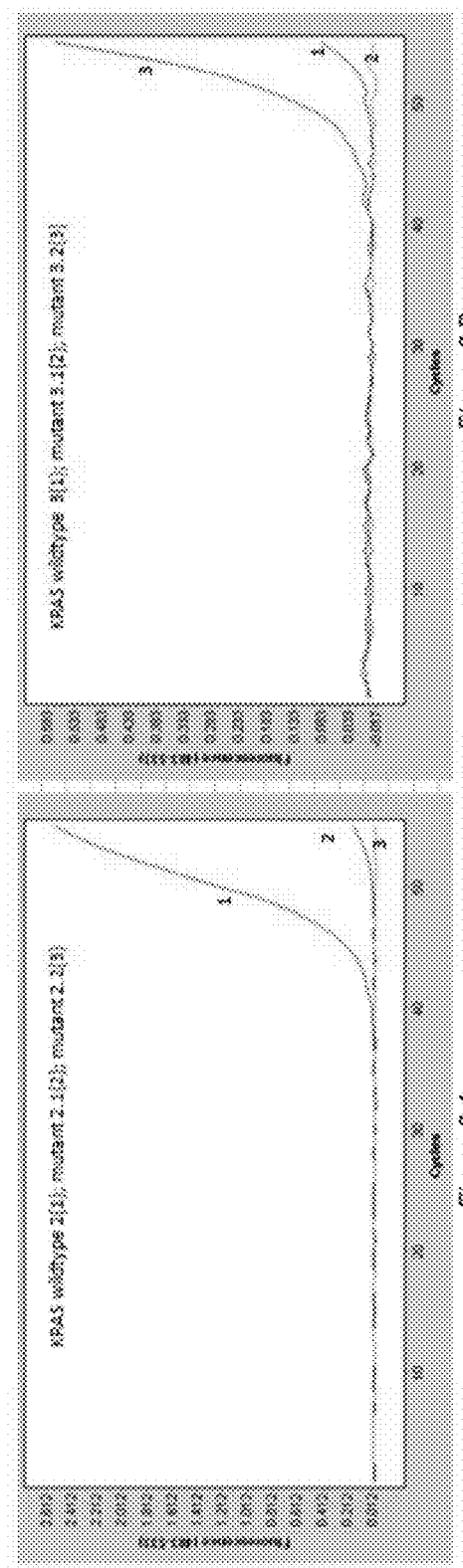
FIG. 8 illustrates an amplification plot for bisulfite converted SW620 cell line DNA. (A) wild-type KRAS assay "1", KRAS mutant 2.1 assay "2", and KRAS mutant 2.2 assay "3". (B) wild-type KRAS assay "1", KRAS mutant 3.1 assay "2", and KRAS mutant 3.2 assay "3".
Figure 9:
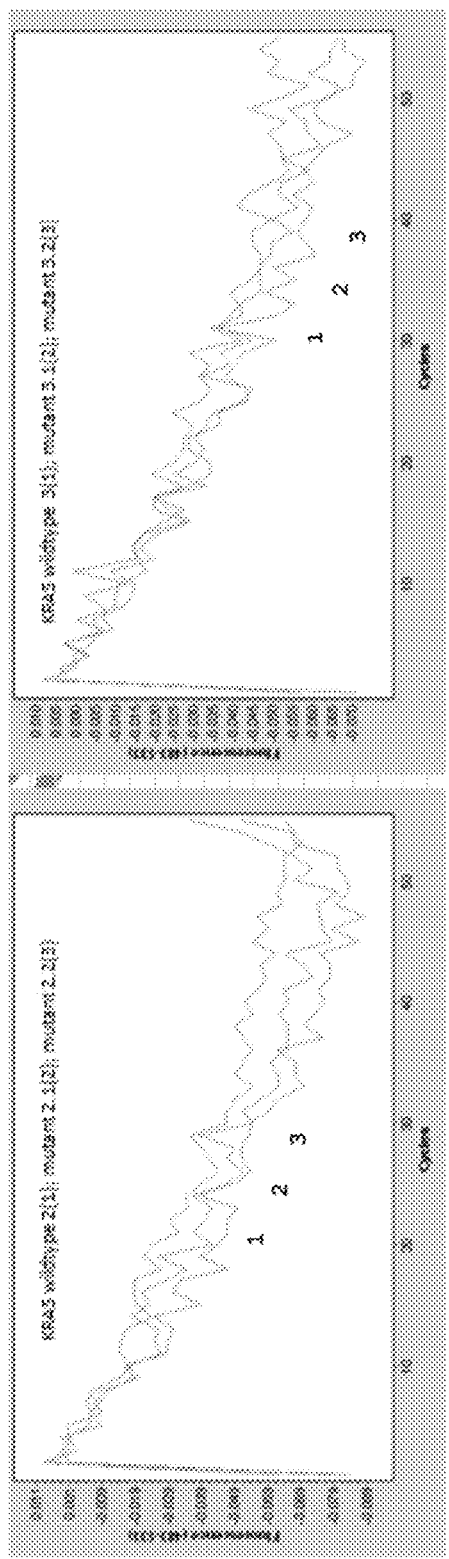
FIG. 9 illustrates an amplification plot for non-bisulfite converted SW260 cell line DNA. (A) wild-type KRAS assay "1", KRAS mutant 2.1 assay "2". and KRAS mutant 2.2 assay "3". (B) wild-type KRAS assay "1", KRAS mutant 3.1 assay "2", and KRAS mutant 3.2 assay "3".

Results: FIG. 6 shows that the wild-type 2 and wild-type 3 assay gave a positive amplification signal on HCT116 bisulfite converted DNA. As shown in FIG. 7, all tested assays scored negative on HCT116 non-bisulfite converted DNA As shown in FIG. 8, the wild-type 2 assay scored positive on SW620 bisulfite converted DNA. The wild-type 3 assay was negative on SW620 BT but the mutant 3.2 assay scored positive on SW620 BT. As shown in FIG. 9, all tested assays tested negative on SW620 non-bisulfite converted DNA.

Figure 10:
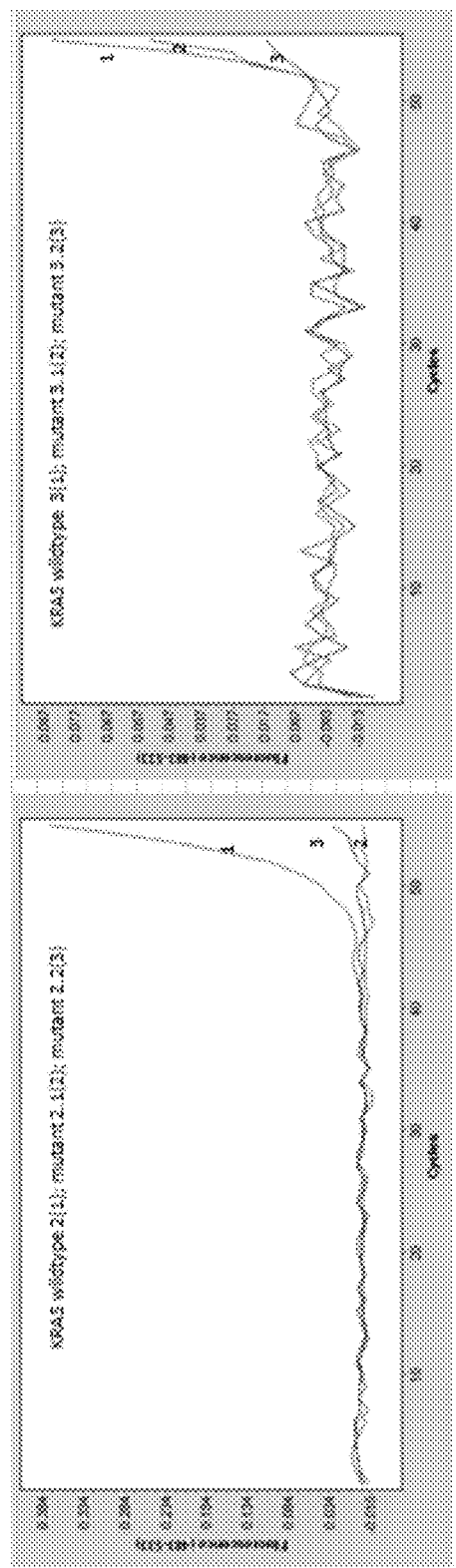
FIG. 10 illustrates an amplification plot for positive control KRAS DNA, bisulfite converted. (A) wild-type KRAS assay "1"; KRAS mutant 2.1 assay "2", and KRAS mutant 2.2 assay "3". (B) wild-type KRAS assay "1", KRAS mutant 3.1 assay "2", and KRAS mutant 3.2 assay "3".
Figure 11:
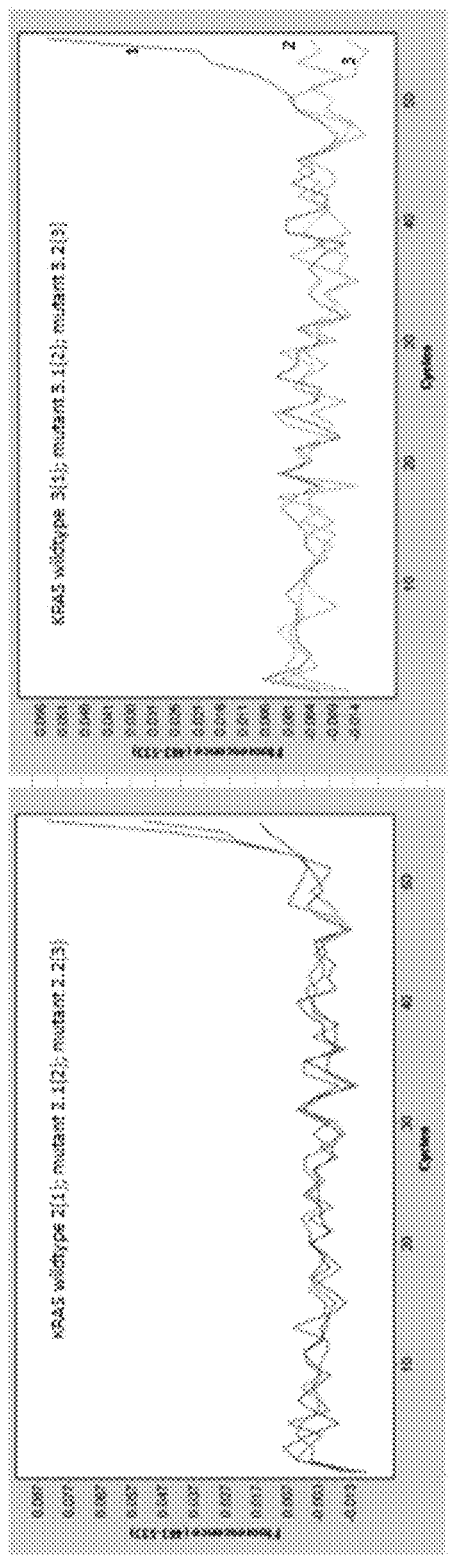
FIG. 11 illustrates an amplification plot for positive control KRAS DNA, non-bisulfite converted. (A) wild-type KRAS assay "1", KRAS mutant 2.1 assay "2", and KRAS mutant 2.2 assay "3". (B) wild-type KRAS assay "1", KRAS mutant 3.1 assay "2", and KRAS mutant 3.2 assay "3".

FIG. 10 shows that all tested assays were negative on positive control Bisulfite converted (BT) DNA (=positive control included in the KRAS Therascreen PCR Kit, Qiagen). All tested assays scored negative on positive control non Bisulfite converted DNA (KRAS Therascreen PCR Kit, Qiagen) as shown in FIG. 11.

Figure 12:
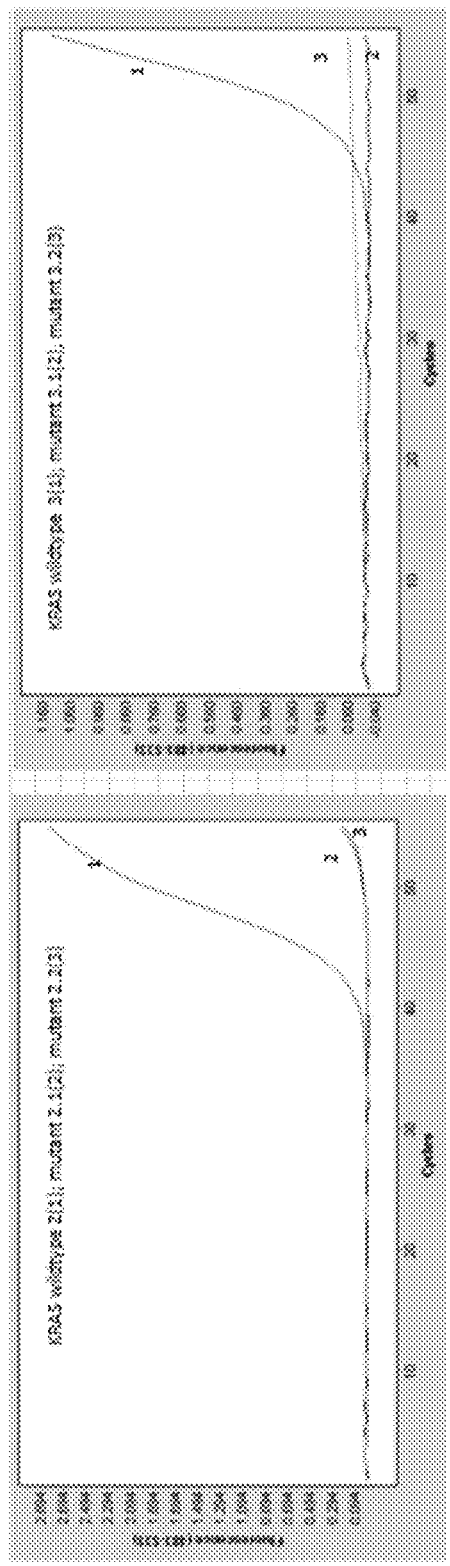
FIG. 12 illustrates an amplification plot for in vitro methylated KRAS DNA (KRAS Therascreen PCR kit, Qiagen), bisulfite converted. (A) wild-type KRAS assay "1", KRAS mutant 2.1 assay "2", and KRAS mutant 2.2 assay "3". (B) wild-type KRAS assay KRAS mutant 3.1 assay "2", and KRAS mutant 3.2 assay "3".
Figure 13:
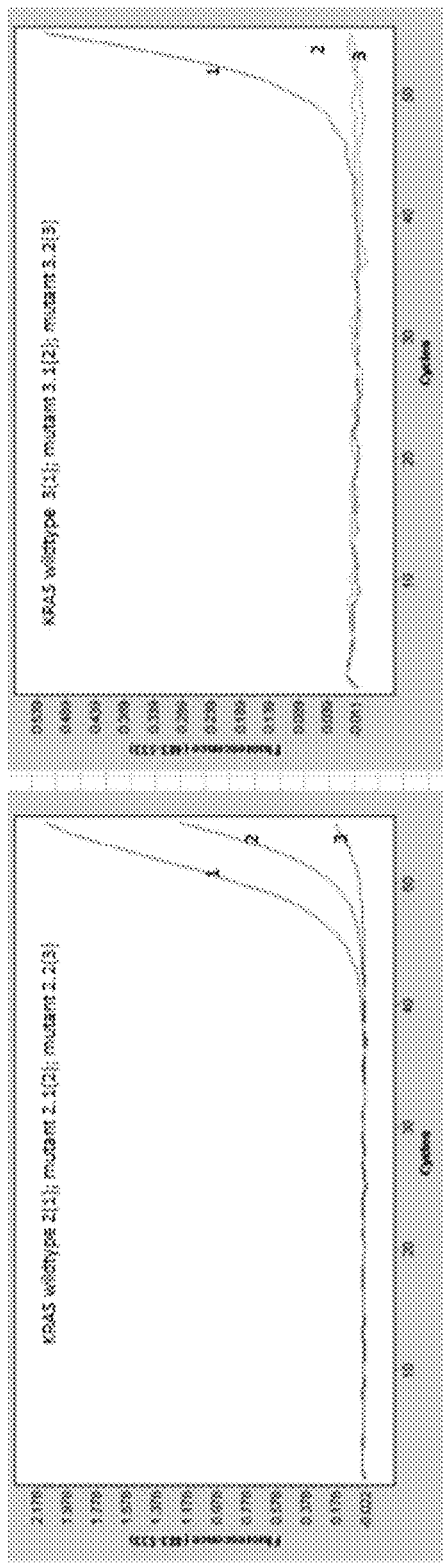
FIG. 13 illustrates an amplification plot for in vitro methylated DKO cell line DNA, bisulfite converted. (A) wild-type KRAS assay "1". KRAS mutant 2.1 assay "2", and KRAS mutant 2.2 assay "3". (B) wild-type KRAS assay "1", KRAS mutant 3.1 assay "2", and KRAS mutant 3.2 assay "3".

As shown in FIG. 12, only the wild-type assays were positive on in vitro methylated BT DNA. Wild-type assays were positive on DKO 8T DNA. However, some background (primer dimers) for mutant 2.1 and 2.2 were detected as shown in FIG. 13.

Primer dimers were detected in NTC as shown in FIG. 14.

Caliper LC90 Results

Figure 15:
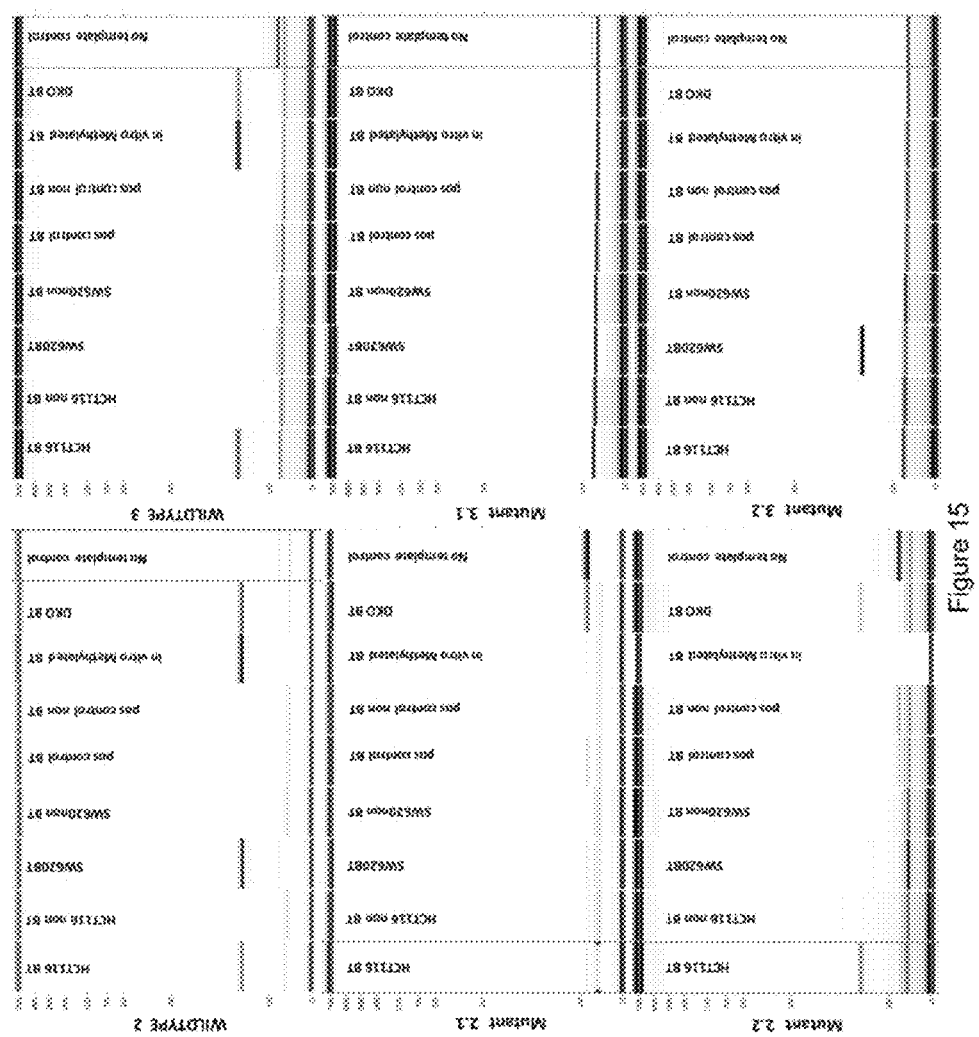
FIG. 15 illustrates gel electrophoresis separation of the amplified products for FIGS. 6-14.

After PCR reactions all reactions were load on the LC90, an electrophoresis system to confirm presence or absence of a specific product. The results are shown in FIG. 15.

Conclusions

No amplification product is obtained for the non-bisulfite converted DNA of HCT116 and SW620 with the designed KRAS mutation primers. Thus, the KRAS MUT-PRIMERS as designed were specific for bisulfite converted DNA. Using bisulfite converted in vitro Methylated DNA template amplification was observed only for the KRAS wild-type assay. With bisulfite converted DKO DNA template, amplification was observed for the wild-type assays, and also a slightly band (amplification signal) with the KRAS mutant 2.2 assay.

SW620 is described in literature as a carrier of mutation 3.2. A clear amplification band with the KRAS mutation 3.2 assay on SW620 bisulfite treated DNA was observed, but no signal was obtained with the KRAS wild-type 3 assay on SW620 bisulfite treated DNA. Thus we were able to detect mutation 3.2 in bisulfite converted DNA of SW620. The HCT116 cell line doesn't carry this mutation, amplification with the KRAS wild-type 3 assay was observed, but not with the KRAS mutant assays.

Methylation Detection

TABLE 7

Designed primers for P16 methylation detection and Beta-Actin detection

| name | Sequence forward | Sequence reverse |
|---|---|---|
| P16_7_14 | TTAGGTAAGGGGACGTCG (SEQ ID NO. 13) | ACCACATTCGCTAAATACTCG (SEQ ID NO. 14) |
| ACTB | TAGGGAGTATATAGGTTG GGGAAGTT (SEQ ID NO. 15) | AACACACAATAACAAACACAA ATTCAC (SEQ ID NO. 16) |

The KRAS mutation testing may be combined with P16 methylation testing, and the BRAF mutation testing may be combined with PTEN methylation testing.

Results for p16

In this experiment P16 gene methylation was tested in cell lines used in the above described experiments for mutation testing (table 2). Generation of Bisulfite treated (BT) DNA was performed as described above. The MSP reactions were performed on the Roche LightCycler 480. The used detector is SYBR green (QuantiTect SYBR Green PCR Kit Qiagen). The used annealing temperature was 57 C, and the number of cycles was 45, during the run 10 cycles were added.

Preparation of Master-Mix:

| Quantitect SYBR green mix (2x) | 5 | 125 |
|---|---|---|
| Forw-Rev Primer Mix (1.25 uM each) | 2 | 50 |
| H2O | 2 | 50 |
| Sample (20 ng/ul) | (1) | Not in the mix |

Nine ul master-mix was dispensed per well in a 384 well plate. One ul of the appropriate sample was added per well.

Data acquisition: Ct on Roche LightCycler 480; Tm on Roche LightCycler 480; Bp, size on Caliper LC90.

Results QPCR, Ct

| | P16_7_14 Assay | | | | ACTB Assay | | | |
|---|---|---|---|---|---|---|---|---|
| | Ct(1) | Ct(2) | Ct(3) | Ct(avg) | Ct(1) | Ct(2) | Ct(3) | Ct(avg) |
| SW620 | 40 | 40 | 40 | | 25.2 | 25.22 | 25.14 | 25.18667 |
| HCT116 | 40 | | | | 26.59 | 25.59 | 25.96 | 26.04667 |
| HT29 | 24.01 | 24.61 | 24.5 | 24.37333 | 23.47 | 23 | 23.29 | 23.18667 |
| Colo205 | | | | | 30.47 | 30.07 | 29.71 | 30.08333 |
| IV M | 25.8 | 25.7 | 26.47 | 25.99 | 25.26 | 24.94 | 24.31 | 24.83667 |
| DKO | | | | | 26 | 26.03 | 26.21 | 26.08 |
| NTC | | | | | 36.89 | | | |

Results QPCR, Tm

| | | P16_7_14 Assay | | | ACTB Assay | | |
|---|---|---|---|---|---|---|---|
| SW260 | Tm1 | 77.32 | 77.32 | 77.36 | 76.51 | 76.63 | 76.61 |
| | Height1 | 0.23 | 0.06 | 0.37 | 1.24 | 1.1 | 1.28 |

-continued

|  |  | P16_7_14 Assay | | | ACTB Assay | | |
| --- | --- | --- | --- | --- | --- | --- | --- |
| HCT116 | Tm1 | 77.13 | 77.14 | 77.18 | 76.66 | 76.58 | 76.59 |
|  | Height1 | 0.12 | 0.01 | 0.04 | 1.33 | 1.22 | 1.32 |
| HT29 | Tm1 | 77.17 | 76.99 | 76.93 | 76.12 | 76.13 | 76.13 |
|  | Height1 | 0.89 | 0.81 | 0.92 | 1.32 | 1.2 | 1.23 |
| Colo25 | Tm1 |  |  |  | 76.05 | 75.99 | 75.98 |
|  | Height1 |  |  |  | 1.08 | 1.11 | 1.09 |
| IV M | Tm1 | 77.22 | 77 | 76.85 | 76.49 | 76.45 | 76.46 |
|  | Height1 | 0.87 | 0.87 | 0.84 | 1.4 | 1.4 | 1.38 |
| DKO | Tm1 |  | 76.81 |  | 75.96 | 76.01 | 76.02 |
|  | Height1 |  | 0 |  | 1.25 | 1.23 | 1.17 |
| NTC | Tm1 |  |  |  | 76.54 |  |  |
|  | Height1 |  |  |  | 1.1 |  |  |

Caliper LC90 Results

Figure 16:
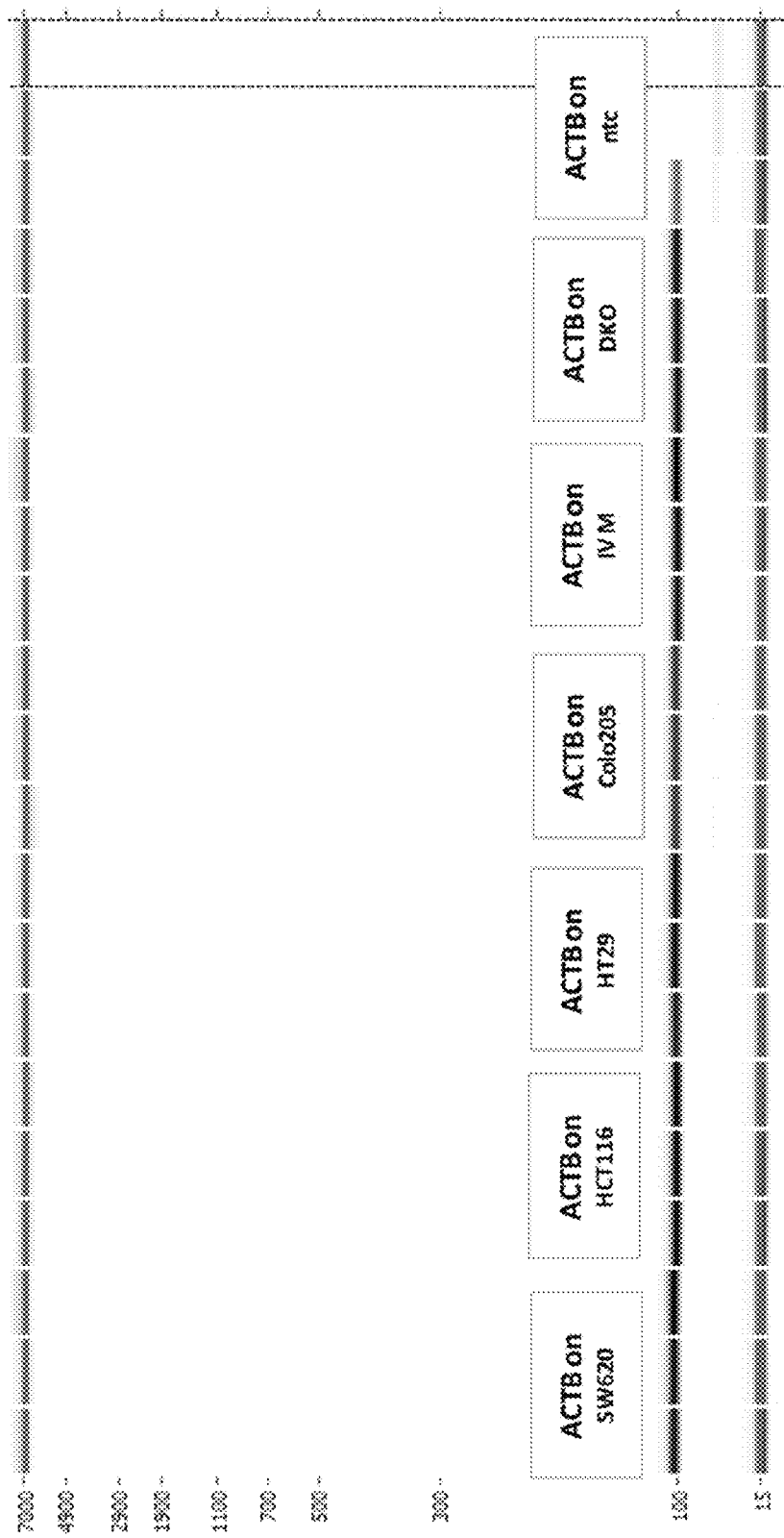
FIG. 16 illustrates gel electrophoresis separation of the amplified products for the ACTS assay as performed on DNA from cell lines SW620, HCT116, HT29, Colo205, as well as in vitro methylated DNA, DNA from the DKO cell line, and non-template DNA.
Figure 17:
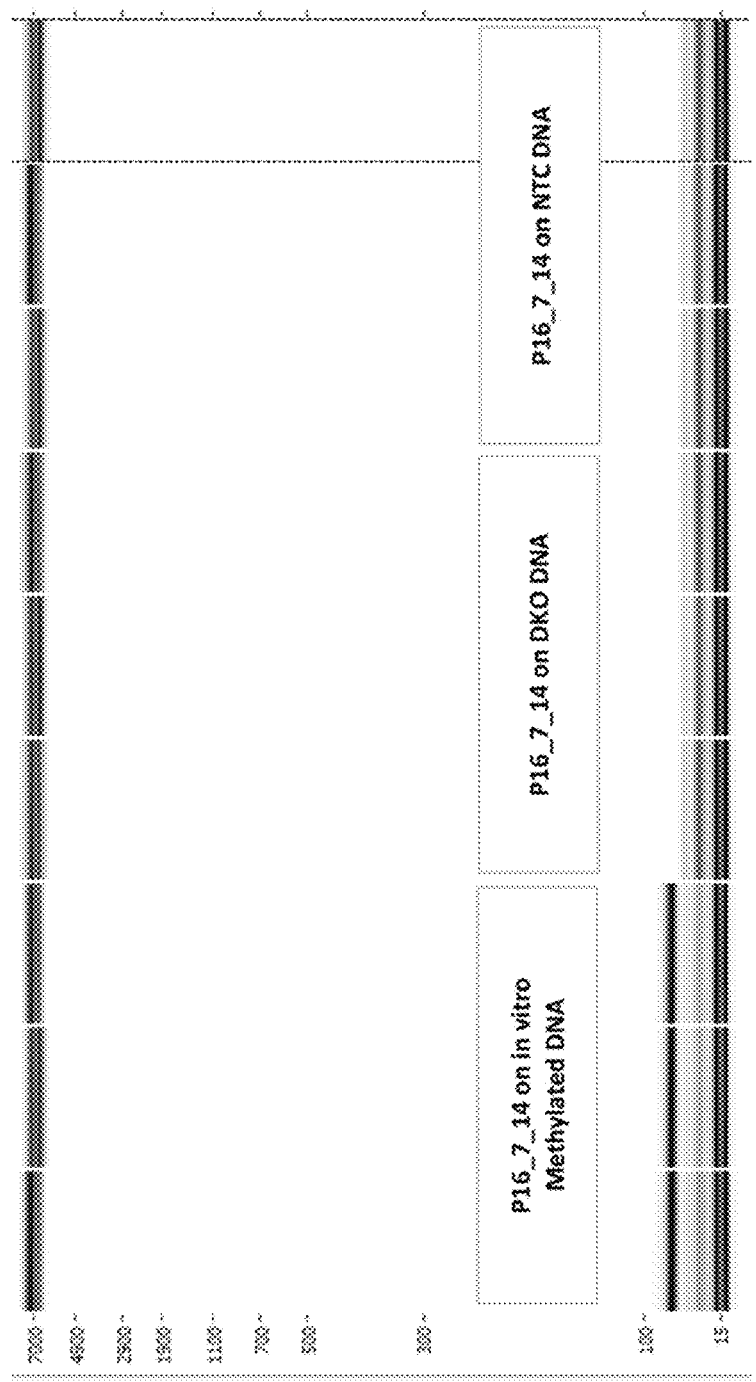
FIG. 17 illustrates gel electrophoresis separation of the amplified products for the P16_7_14 assay as performed on in vitro methylated DNA, DNA from the DKO cell line, and non-template DNA.
Figure 18:
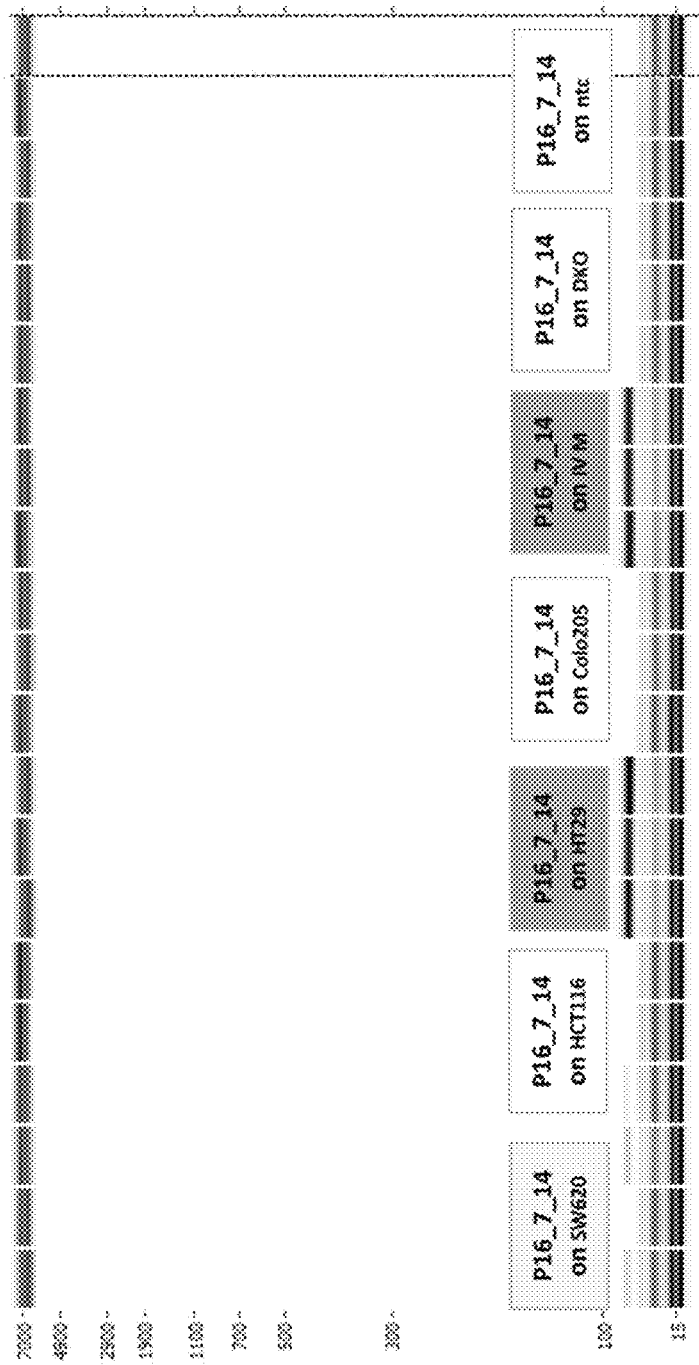
FIG. 18 illustrates gel electrophoresis separation of the amplified products for the P16_7_14 assay as performed on DNA from cell lines SW620, HCT116, HT29, Colo205, as well as in vitro methylated DNA, DNA from the DKO cell line, and non-template DNA.
Figure 19:
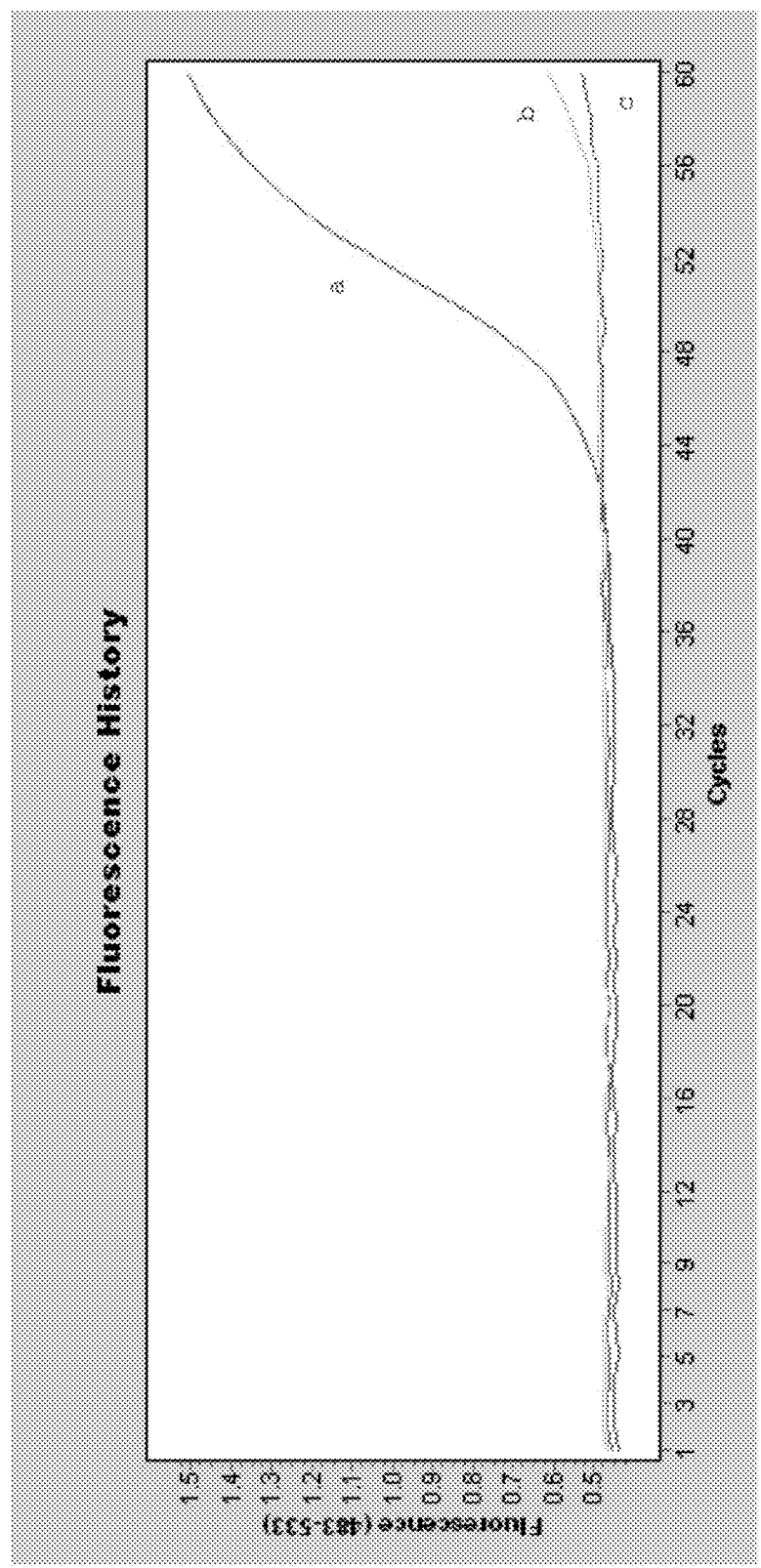
FIG. 19 illustrates an amplification plot of the wild-type KRAS assay "a", the KRAS mutant 3.1 assay "b", and the KRAS mutant 3.2 assay "c", as performed on bisulfite converted in vitro methylated KRAS DNA.
Figure 20:
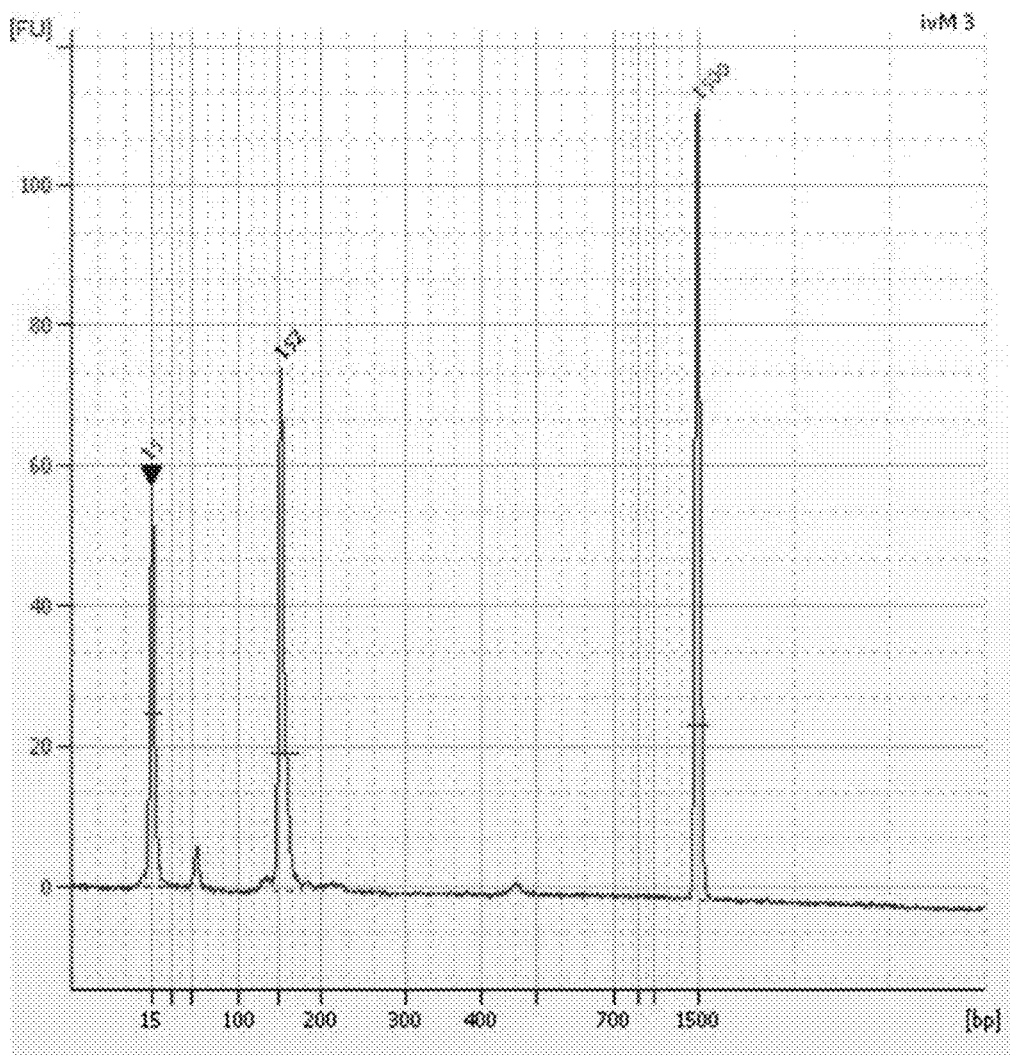
FIG. 20 illustrates a chromatogram trace of an Agilent Bioanlyser 2100 analysis of the amplified product "a" of FIG. 19. The first peak (15) represents the lower marker with a length of 15 bp. The third peak represents the uppermarker (1500) with a length of 1500 bp. The middle peak represents the specific PCR product amplified with the wild-type primers.
Figure 21:
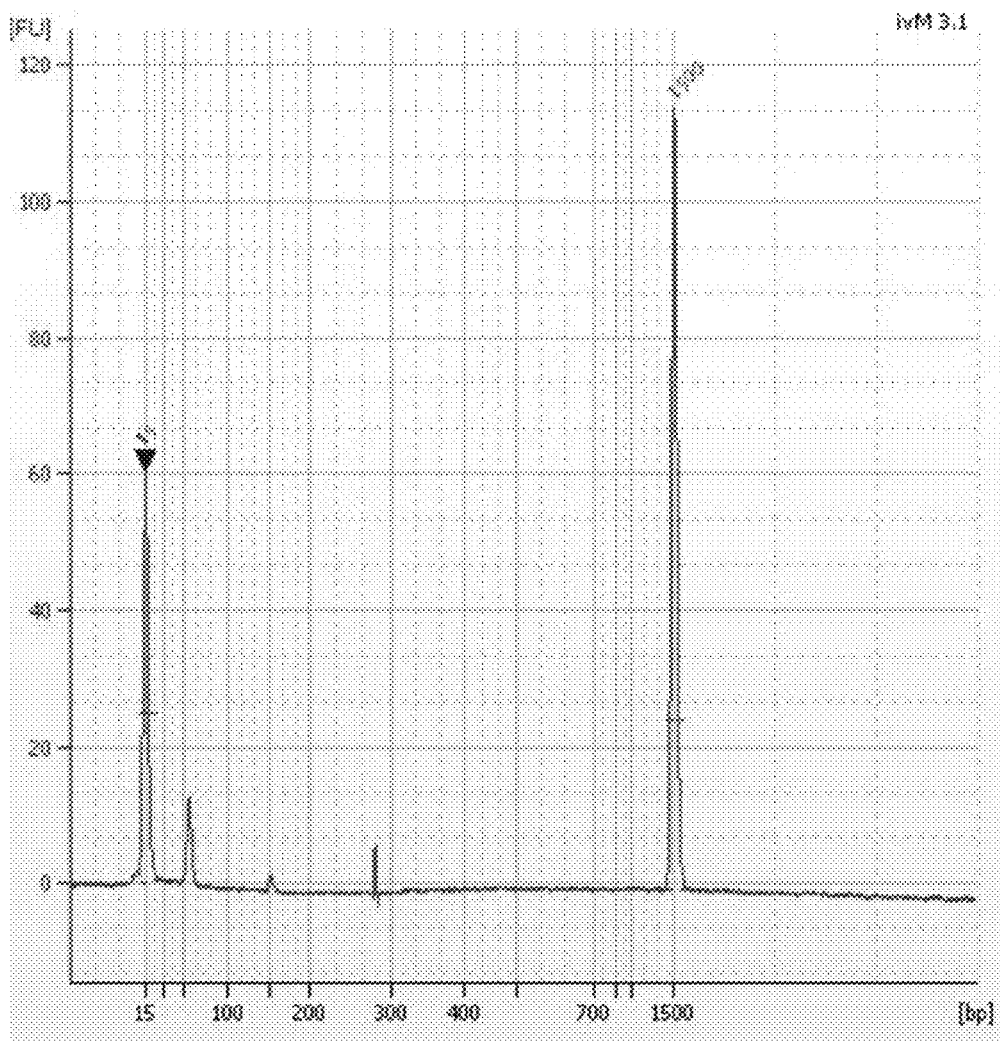
FIG. 21 illustrates a chromatogram trace of an Agilent Bioanlyser 2100 analysis of the amplified product "b" of FIG. 19. The first peak (15) represents the lower marker with a length of 15 bp. The third peak represents the uppermarker (1500) with a length of 1500 bp. There is no significant peak between the upper and lower marker, which means there is no amplification with mutant 3.1 primers.
Figure 22:
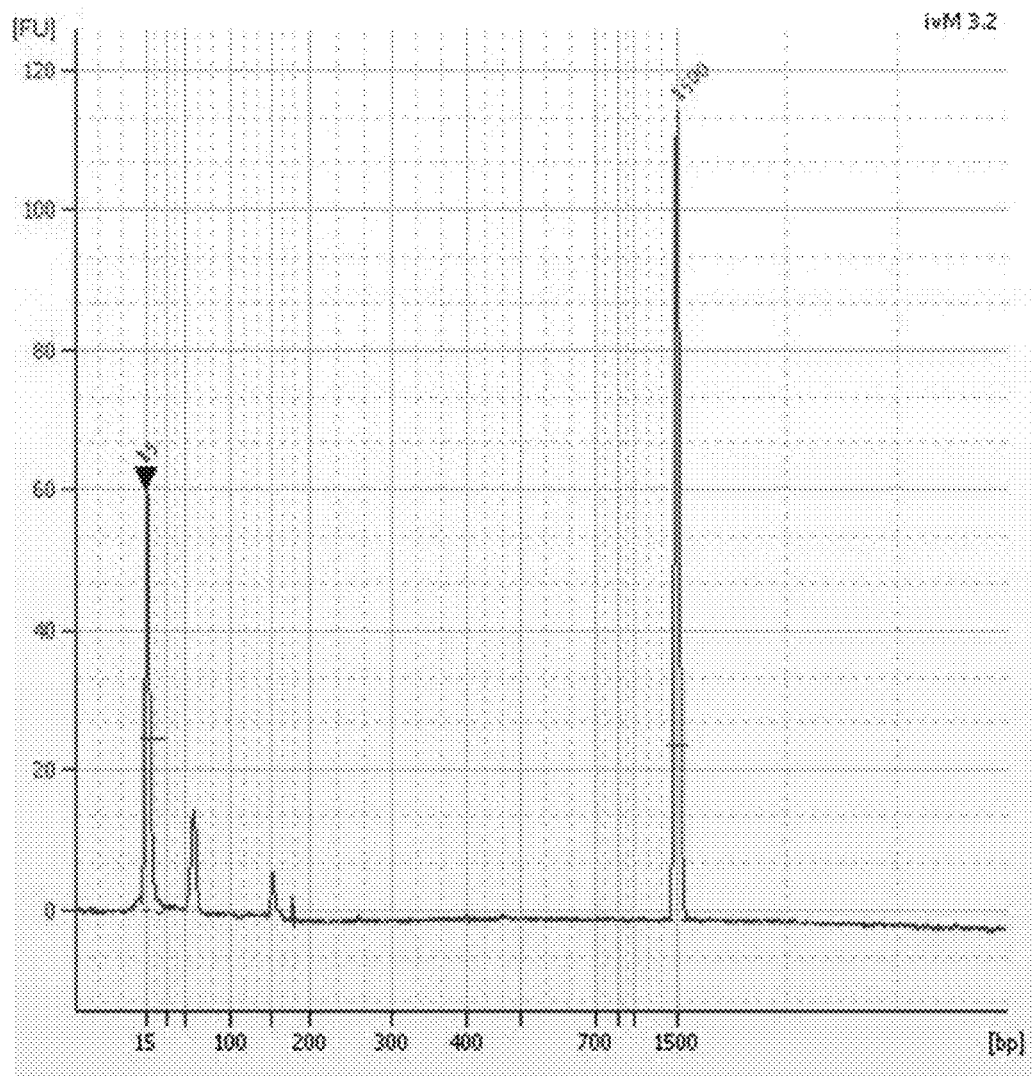
FIG. 22 illustrates a chromatogram trace of an Agilent Bioanlyser 2100 analysis of the amplified product "c" of FIG. 19. The first peak (15) represents the lower marker with a length of 15 bp. The third peak represents the uppermarker (1500) with a length of 1500 bp. There is no significant peak between the upper and lower marker, which means there is no amplification with mutant 3.2 primers.
Figure 23:
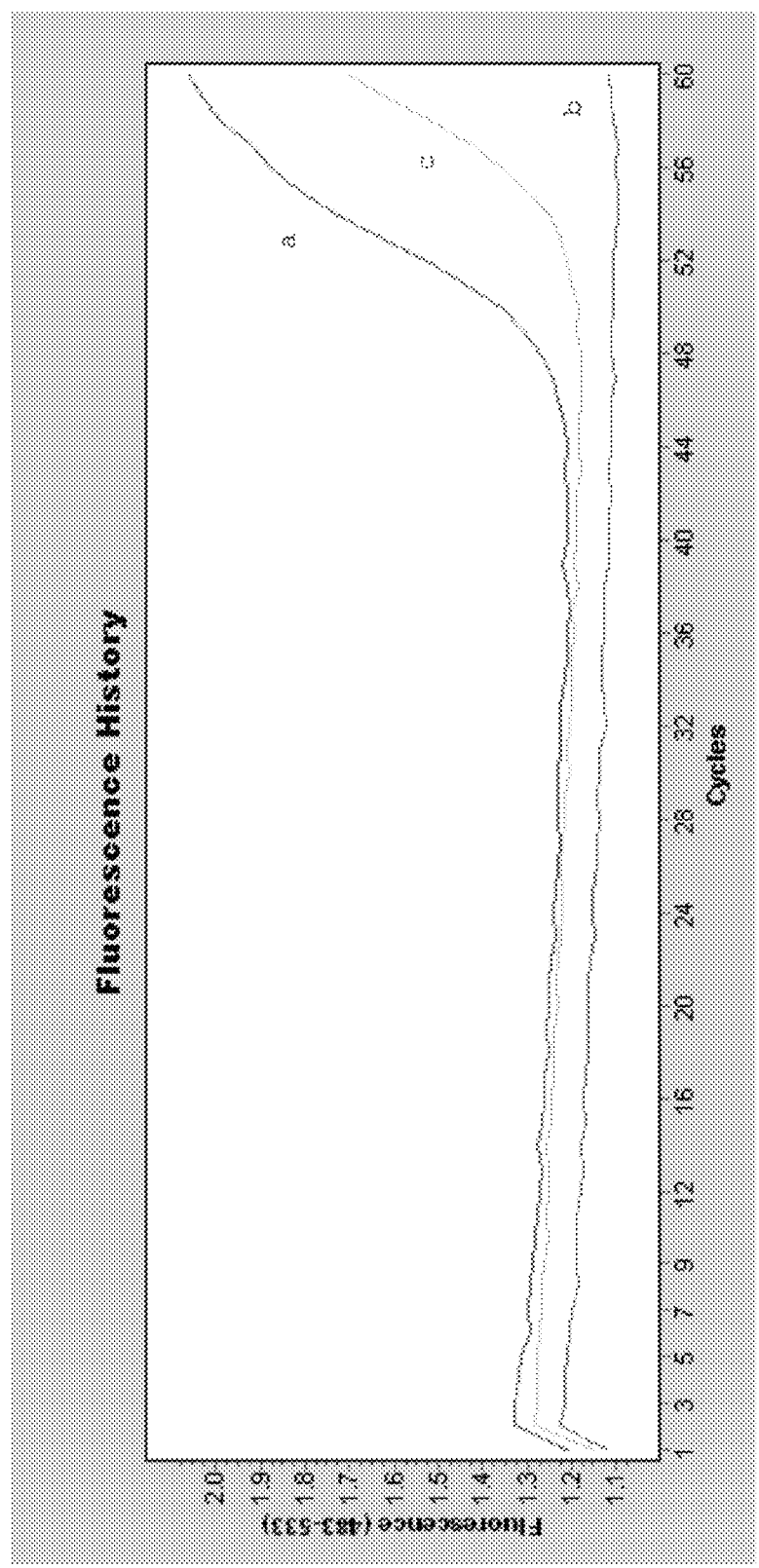
FIG. 23 illustrates an amplification plot of the wild-type KRAS assay "a", the KRAS mutant 3.1 assay "b", and the KRAS mutant 3.2 assay "c", as performed on bisulfite converted primary sample EK11-229 DNA.
Figure 24:
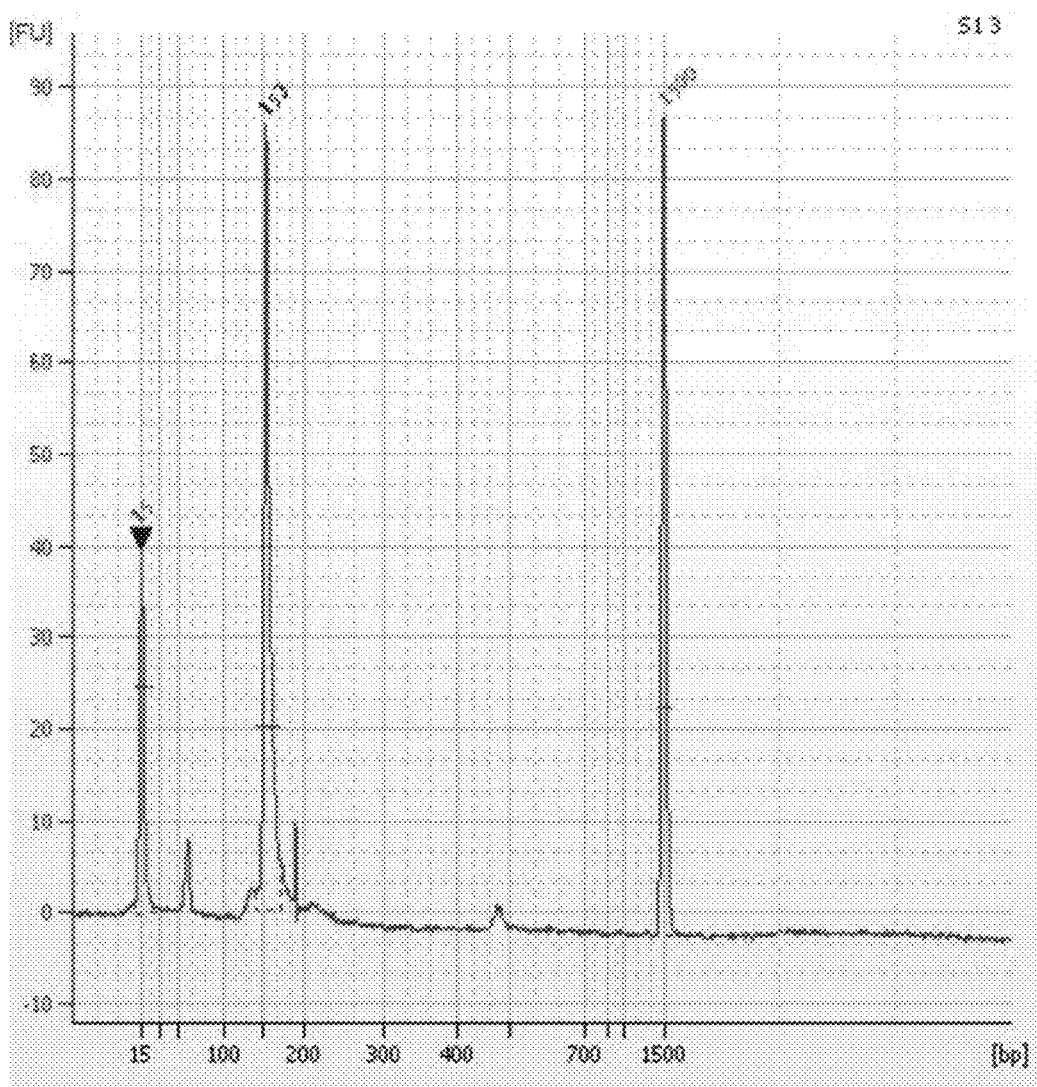
FIG. 24 illustrates a chromatogram trace of an Agilent Bioanlyser 2100 analysts of the amplified product "a" of FIG. 23. The first peak (15) represents the lower marker with a length of 15 bp. The third peak represents the uppermarker (1500) with a length of 1500 bp. The middle peak represents the specific PCR product amplified with the wild-type primers.
Figure 25:
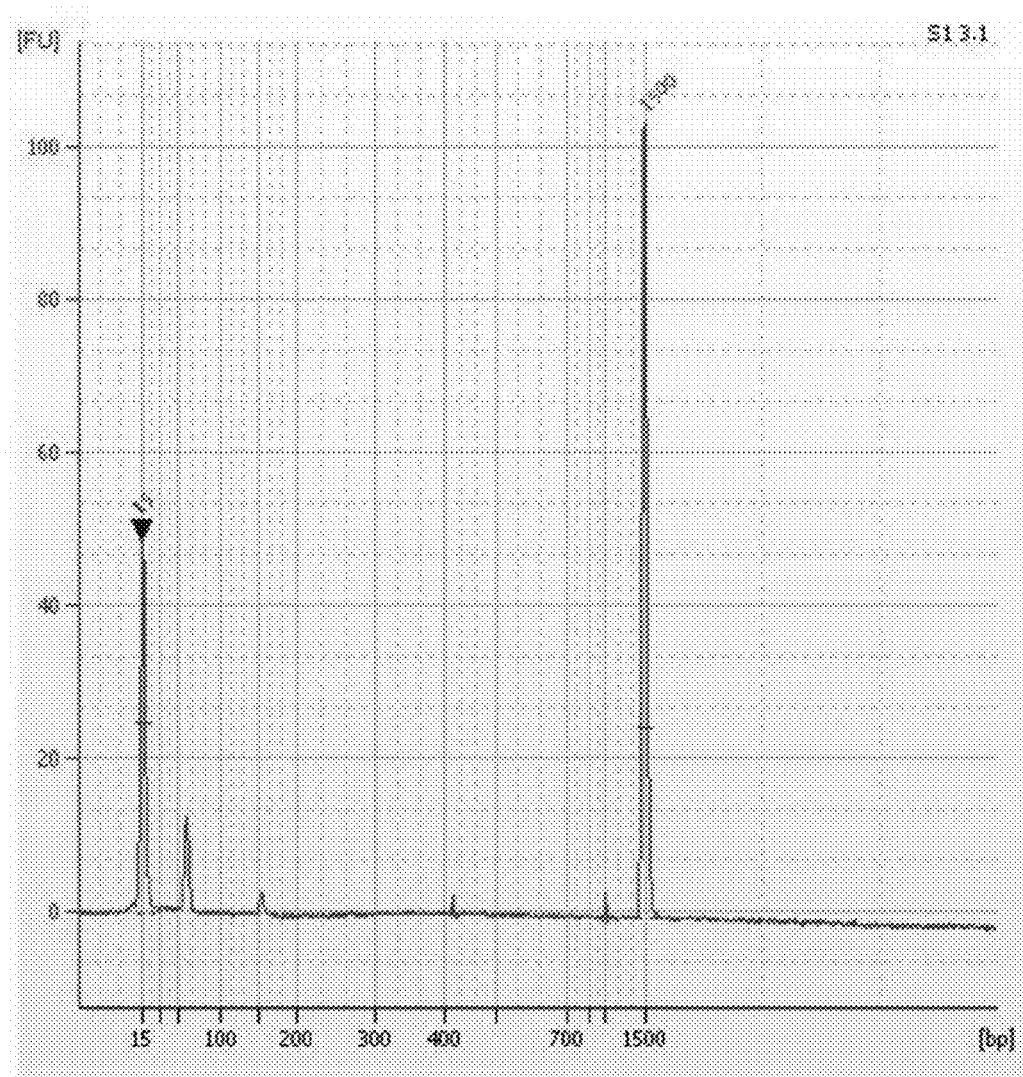
FIG. 25 illustrates a chromatogram trace of an Agilent Bioanlyser 2100 analysis of the amplified product "b" of FIG. 23. The first peak (15) represents the lower marker with a length of 15 bp. The third peak represents the uppermarker (1500) with a length of 1500 bp. There is no significant peak between the upper and lower marker, which means there is no amplification with mutant 3.1 primers.
Figure 26:
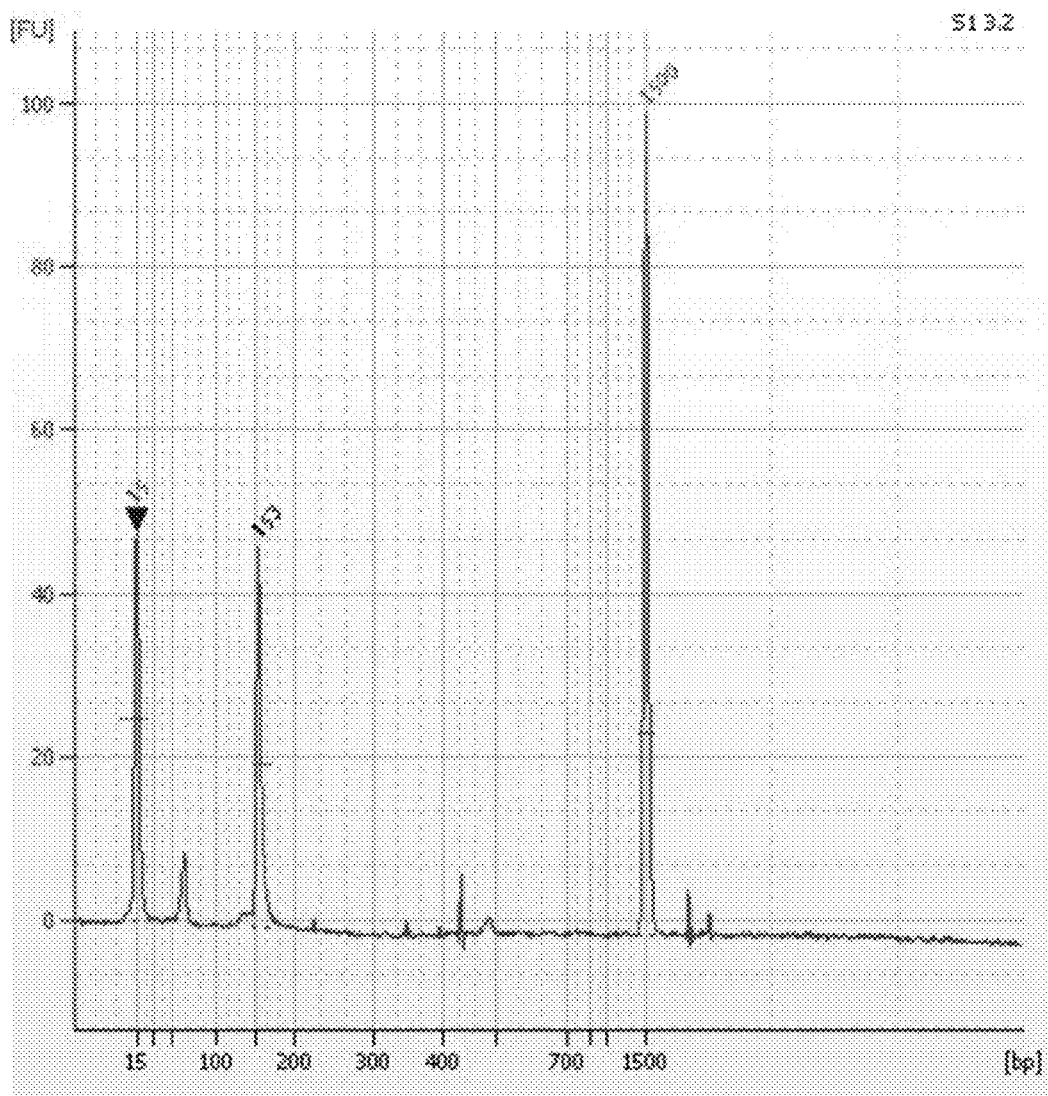
FIG. 26 illustrates a chromatogram trace of an Agilent Bioanlyser 2100 analysis of the amplified product "c" of FIG. 23. The first peak (15) represents the lower marker with a length of 15 bp. The third peak represents the uppermarker (1500) with a length of 1500 bp. There is a significant peak between the upper and lower marker, which means there is amplification with mutant 3.2 primers, and this amplification results in a peak of the expected length of 153 bp.
Figure 27:
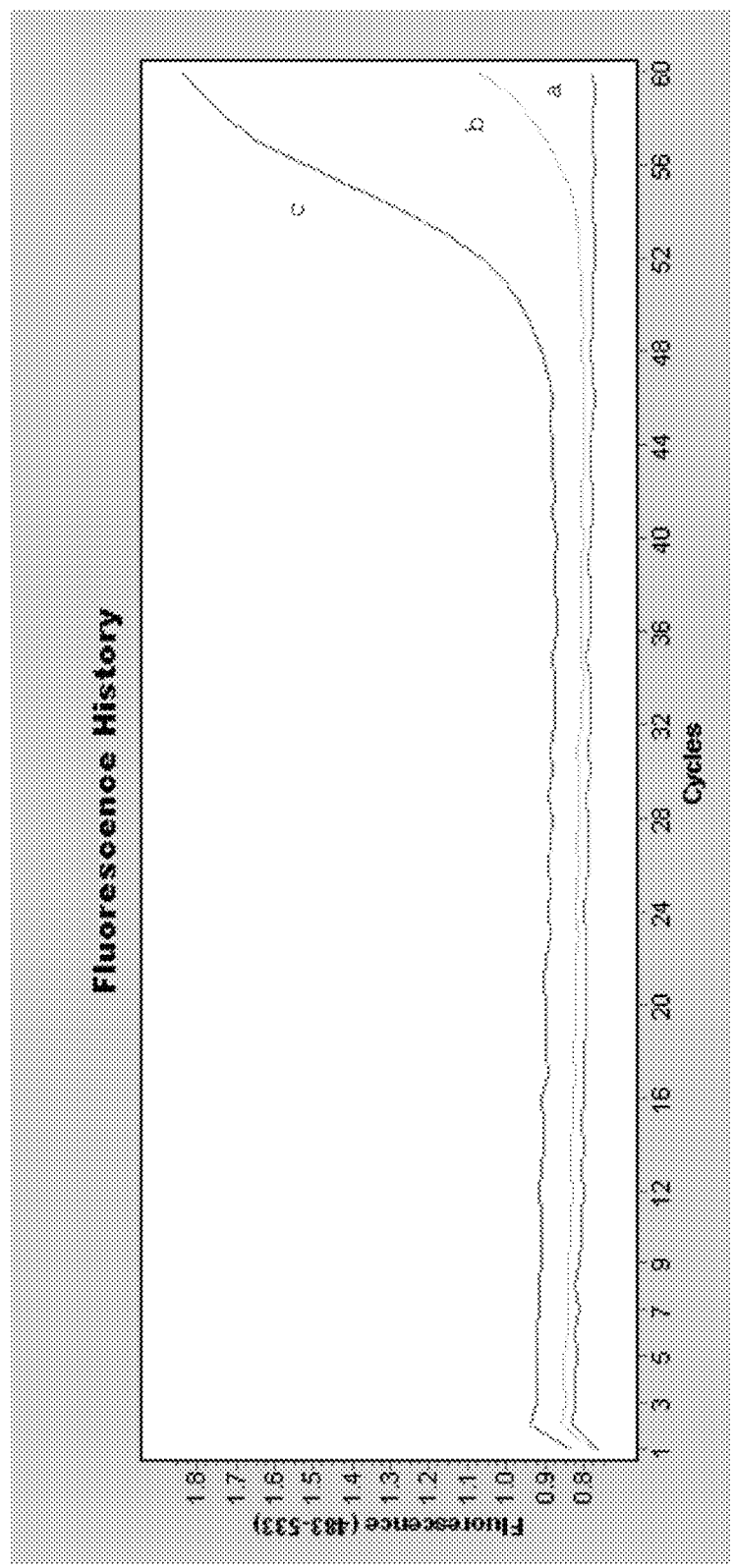
FIG. 27 illustrates an amplification plot of the wild-type KRAS assay "a", the KRAS mutant 3.1 assay "b", and the KRAS mutant 3.2 assay "c", as performed on bisulfite converted primary sample EK11-392 DNA.
Figure 28:
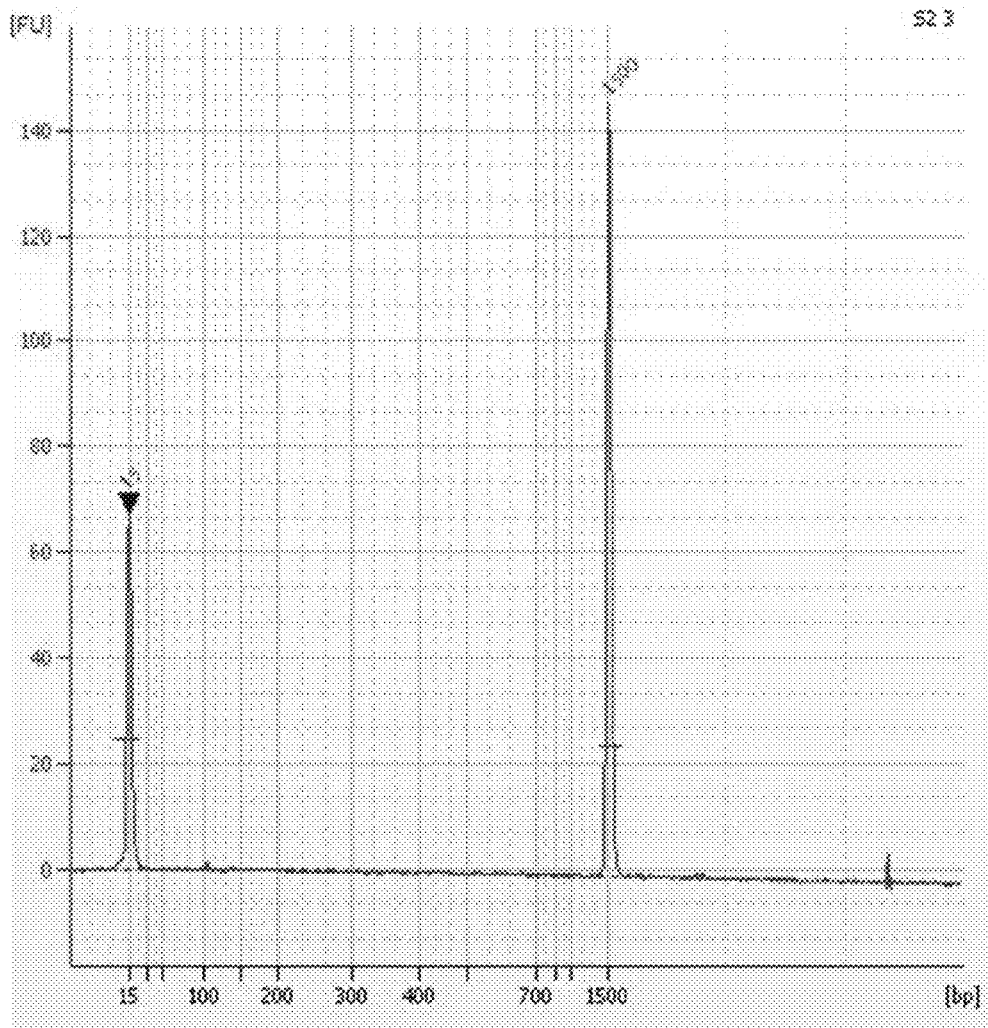
FIG. 28 illustrates a chromatogram trace of an Agilent Bioanlyser 2100 analysis of the amplified product "a" of FIG. 27. The first peak (15) represents the lower marker with a length of 15 bp. The third peak represents the uppermarker (1500) with a length of 1500 bp. There is no middle peak, which indicates that there is no amplification with the wild-type primers.
Figure 29:
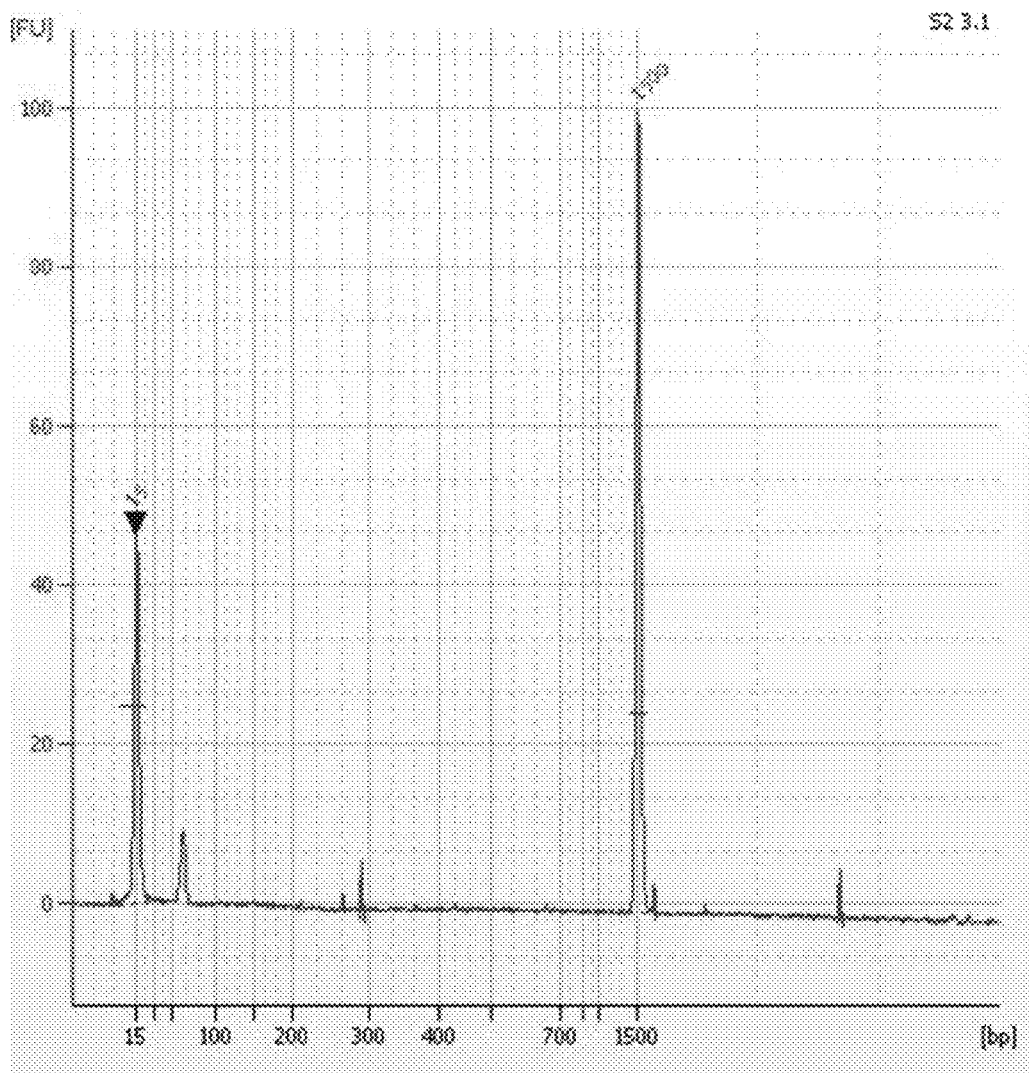
FIG. 29 illustrates a chromatogram trace of an Agilent Bioanlyser 2100 analysis of the amplified product "b" of FIG. 27. The first peak (15) represents the lower marker with a length of 15 bp. The third peak represents the uppermarker (1500) with a length of 1500 bp. There is no significant peak between the upper and lower marker, which means there is no amplification with mutant 3.1 primers.
Figure 30:
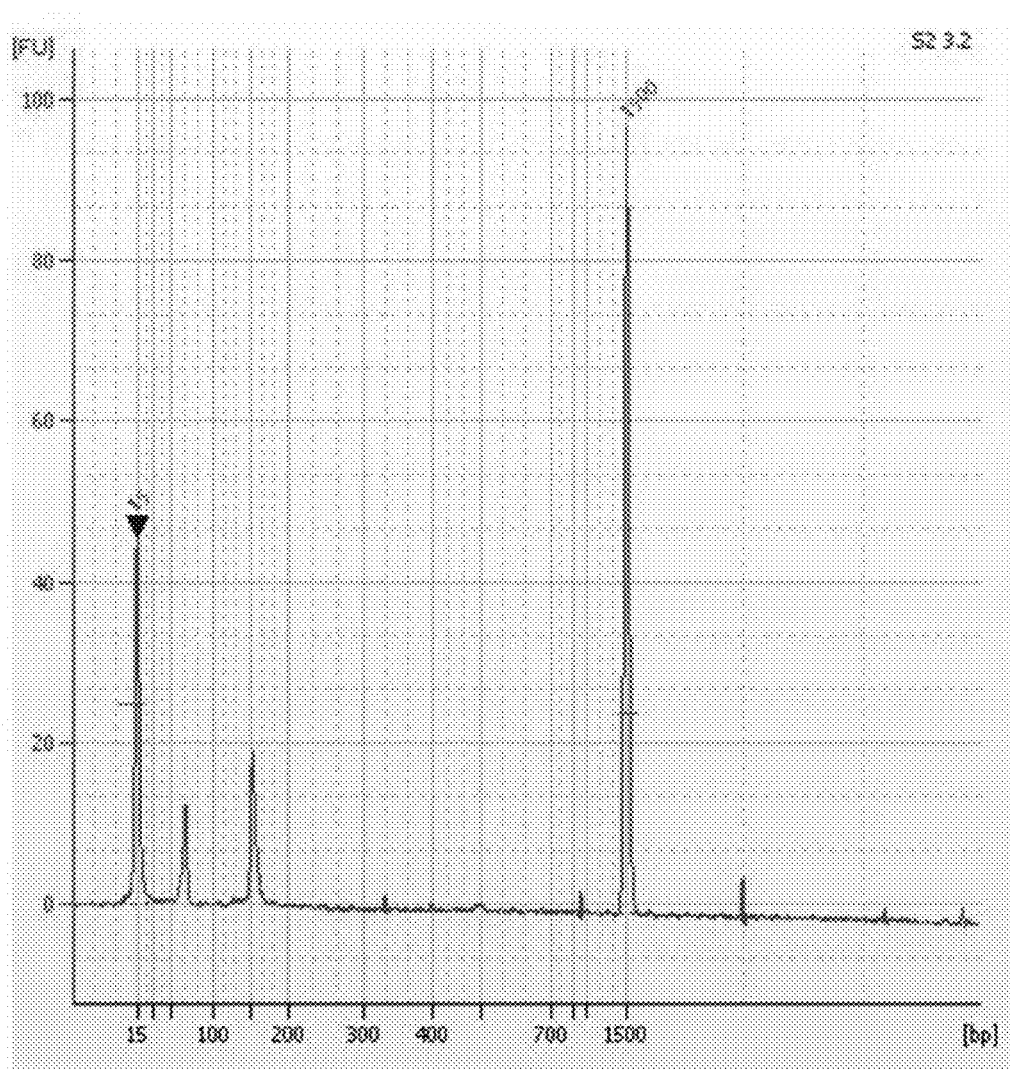
FIG. 30 illustrates a chromatogram trace of an Agilent Bioanlyser 2100 analysis of the amplified product "c" of FIG. 27. The first peak (15) represents the lower marker with a length of 15 bp. The third peak represents the uppermarker (1500) with a length of 1500 bp. There is a significant peak between the upper and lower marker, which means there is amplification with mutant 3.2 primers, and this amplification results in a peak of the expected length of 153 bp.
Figure 31:
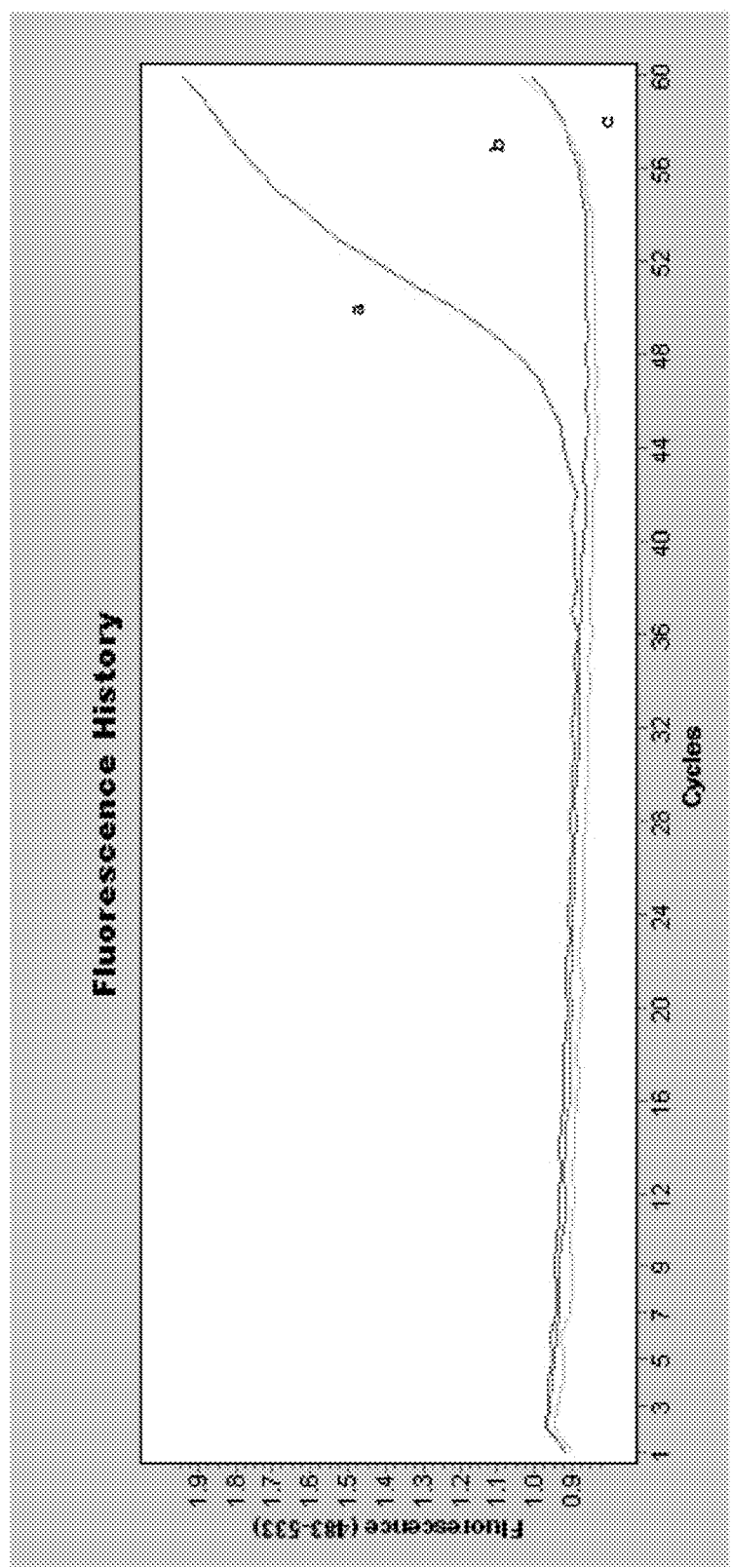
FIG. 31 illustrates an amplification plot of the wild-type KRAS assay "a", the KRAS mutant 3.1 assay "b", and the KRAS mutant 3.2 assay "c", as performed on bisulfite converted primary sample EK12-34 DNA.
Figure 32:
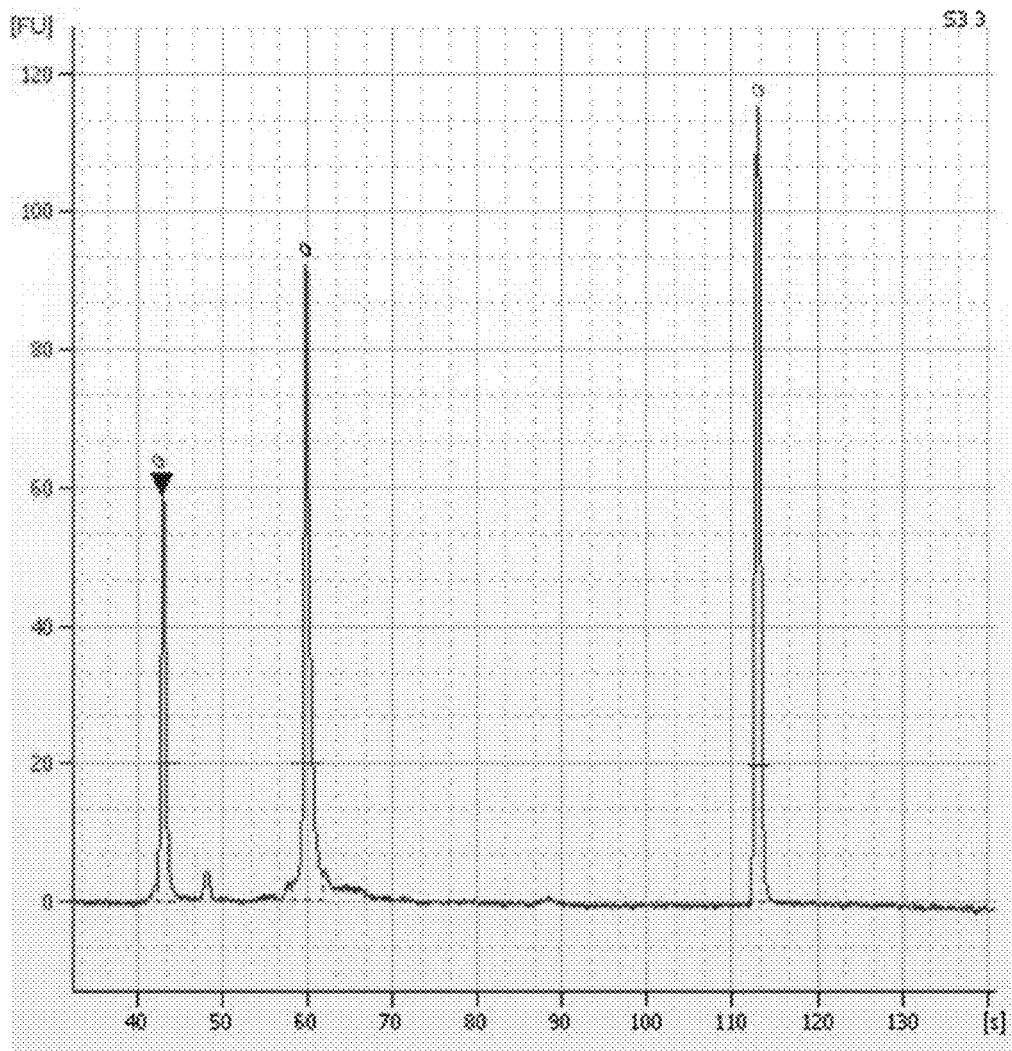
FIG. 32 illustrates a chromatogram trace of an Agilent Bioanlyser 2100 analysis of the amplified product "a" of FIG. 31. The first peak (15) represents the lower marker with a length of 15 bp. The third peak represents the uppermarker (1500) with a length of 1500 bp. The middle peak represents the specific PCR product amplified with the wild-type primers.
Figure 33:
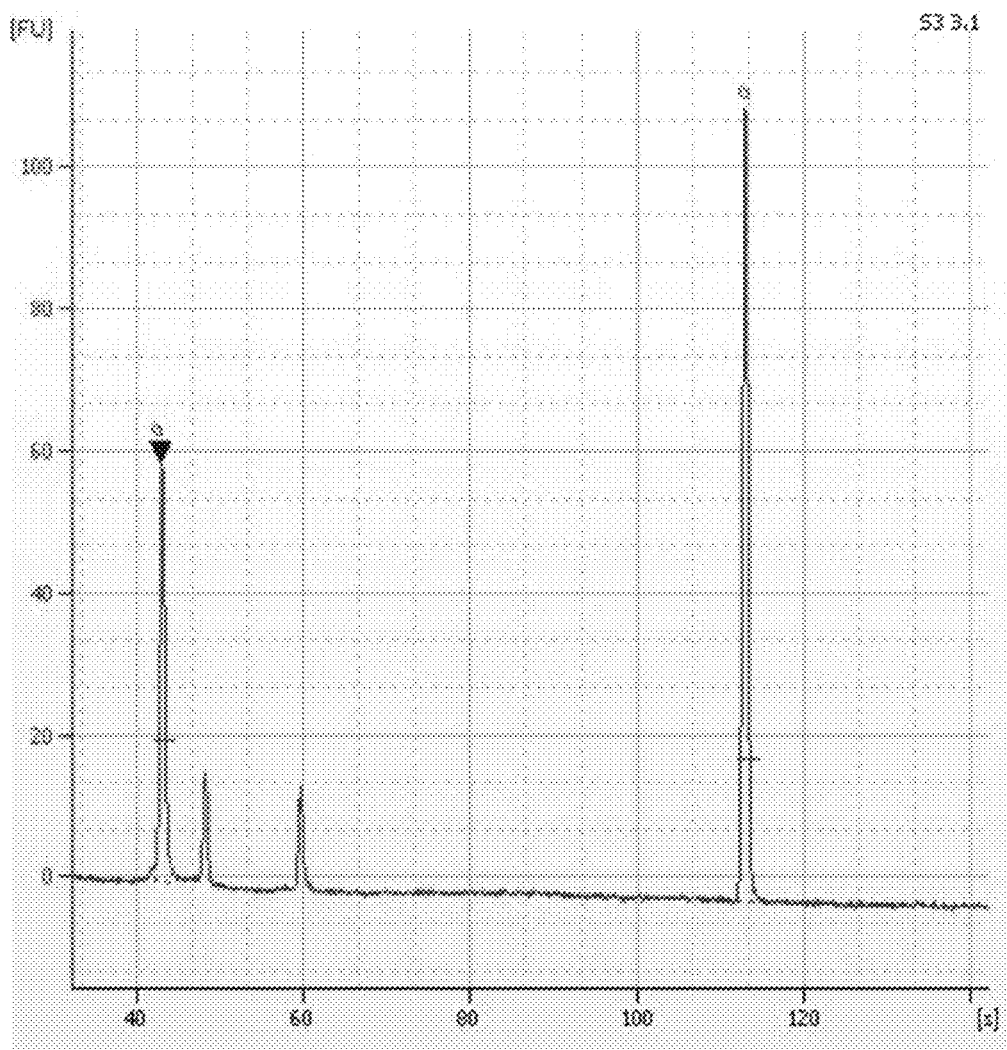
FIG. 33 illustrates a chromatogram trace of an Agilent Bioanlyser 2100 analysis of the amplified product "b" of FIG. 31. The first peak (15) represents the lower marker with a length of 15 bp. The third peak represents the uppermarker (1500) with a length of 1500 bp. A middle peak is observed for mutant 3.1 but with a low amplitude.
Figure 34:
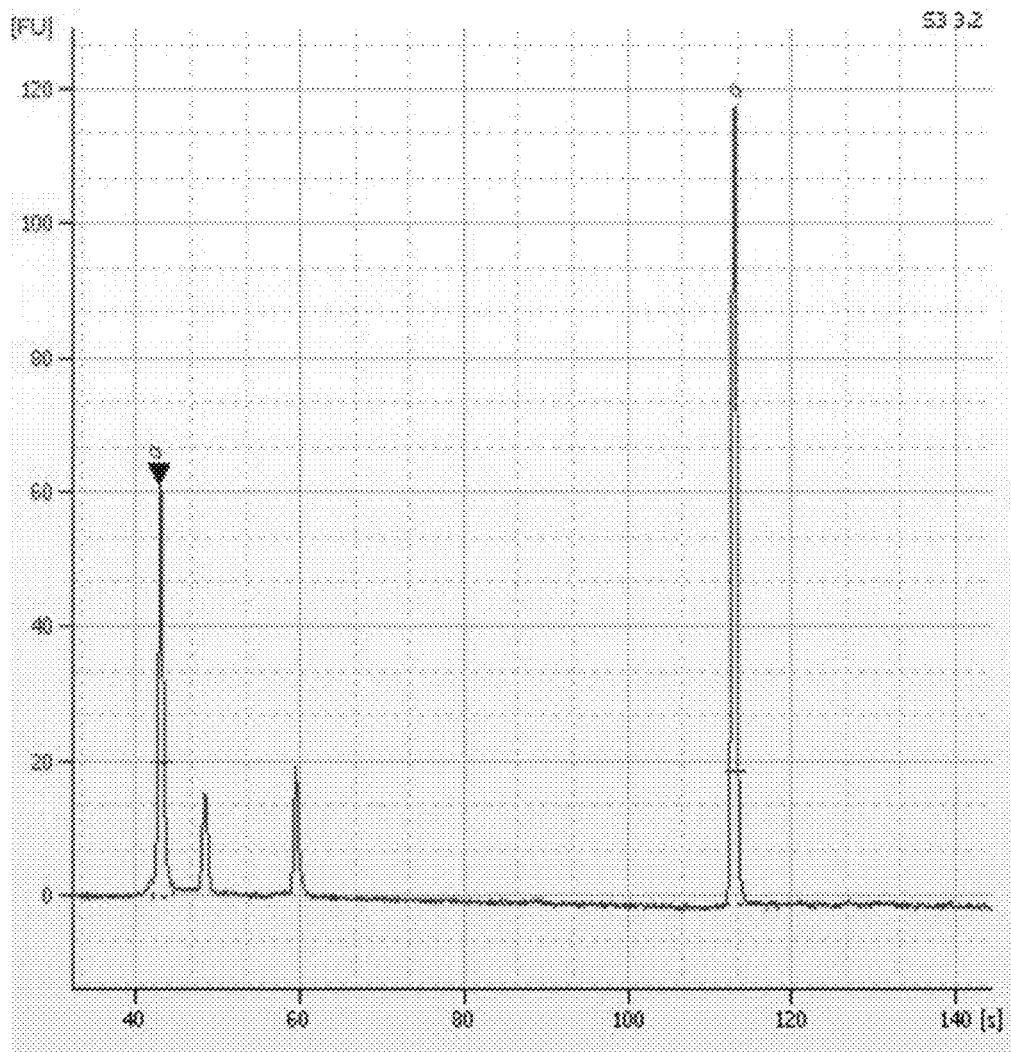
FIG. 34 illustrates a chromatogram trace of an Agilent Bioanlyser 2100 analysis of the amplified product "c" of FIG. 31. The first peak (15) represents the lower marker with a length of 15 bp. The third peak represents the uppermarker (1500) with a length of 1500 bp. A middle peak is observed for mutant 3.2 but with a low amplitude.
Figure 35:
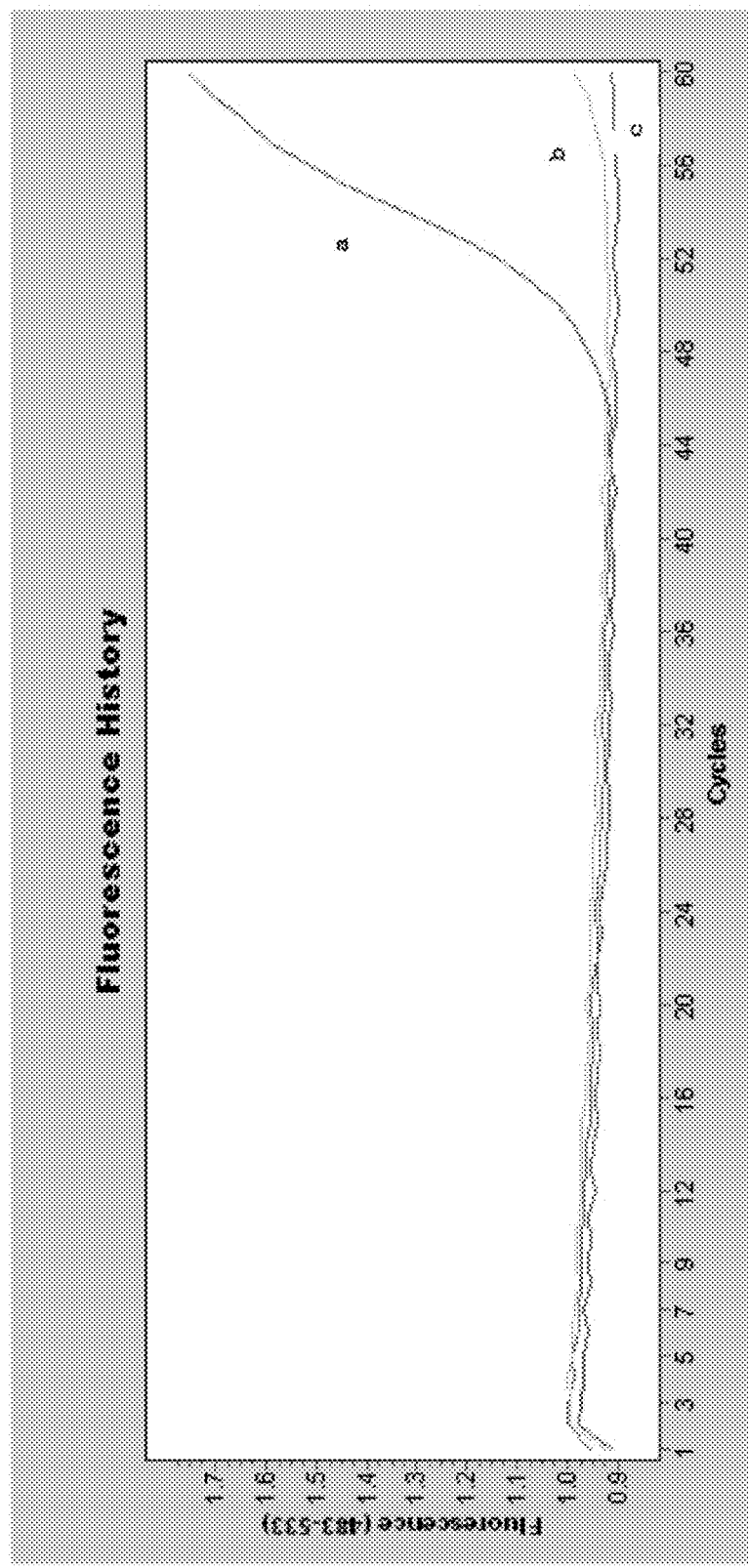
FIG. 35 illustrates an amplification plot of the wild-type KRAS assay "a", the KRAS mutant 3.1 assay "b", and the KRAS mutant 3.2 assay "c", as performed on bisulfite converted primary sample EK12-5 DNA.
Figure 36:
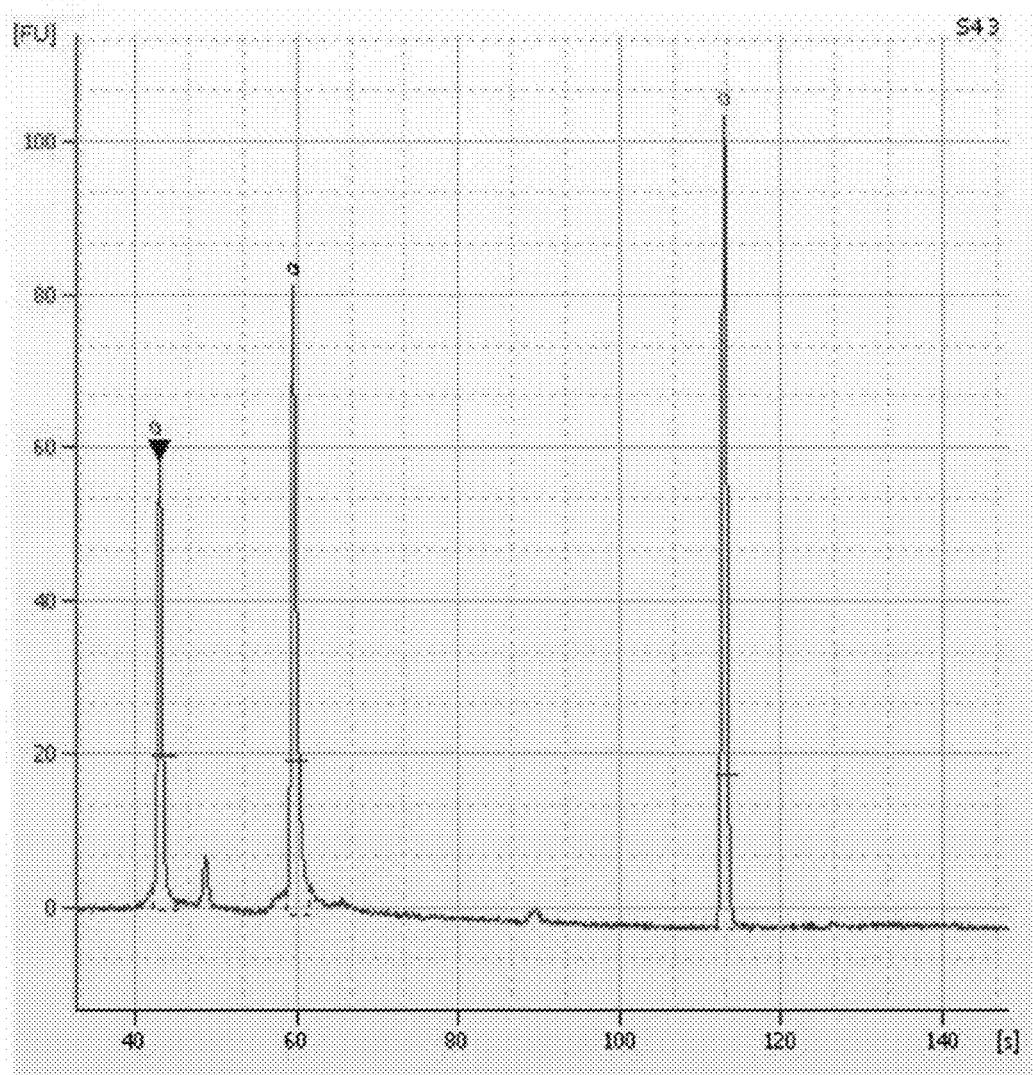
FIG. 36 illustrates a chromatogram trace of an Agilent Bioanlyser 2100 analysis of the amplified product "a" of FIG. 35. The first peak (15) represents the lower marker with a length of 15 bp. The third peak represents the uppermarker (1500) with a length of 1500 bp. The middle peak represents the specific PCR product amplified with the wild-type primers.
Figure 37:
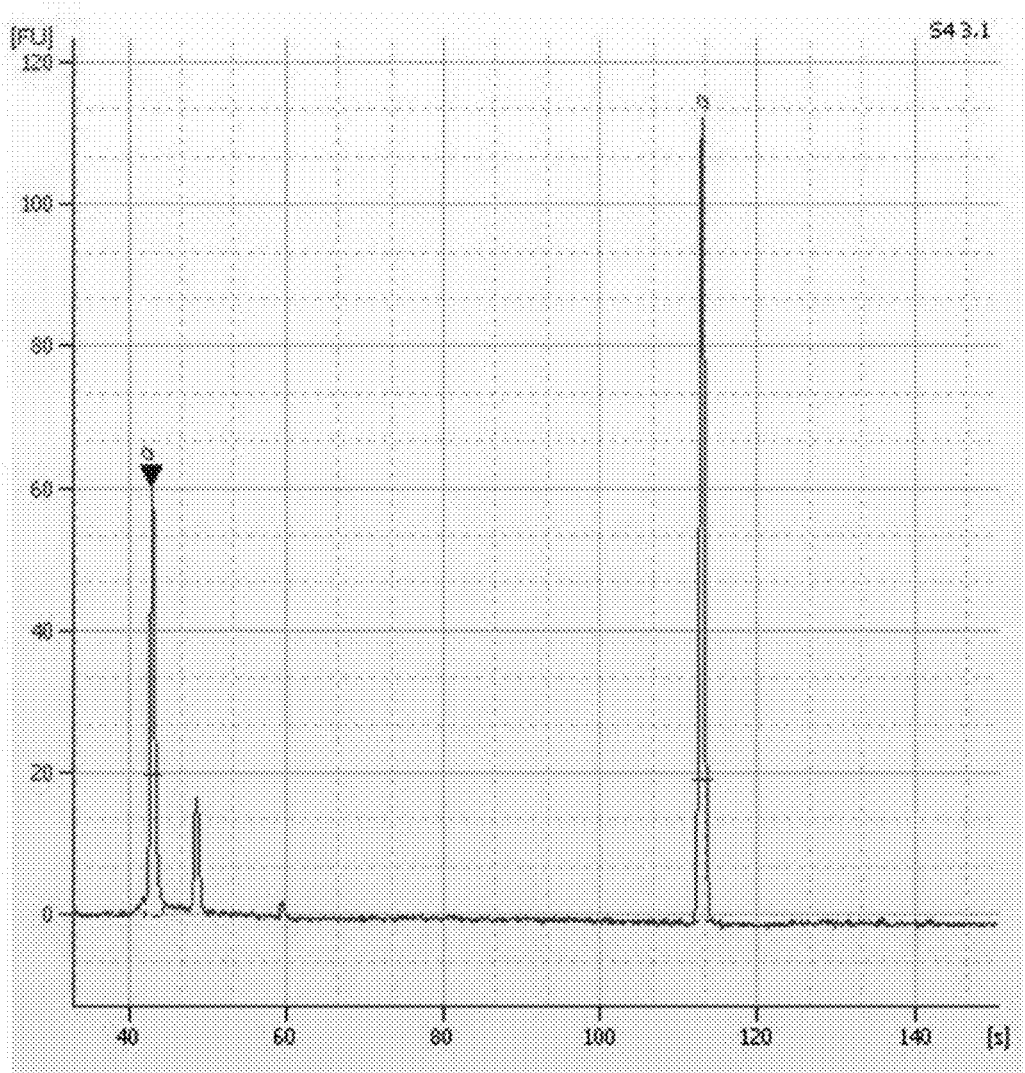
FIG. 37 illustrates a chromatogram trace of an Agilent Bioanlyser 2100 analysis of the amplified product "b" of FIG. 35. The first peak (15) represents the lower marker with a length of 15 bp. The third peak represents the uppermarker (1500) with a length of 1500 bp. There is no significant peak between the upper and lower marker, which means there is no amplification with mutant 3.1 primers.
Figure 38:
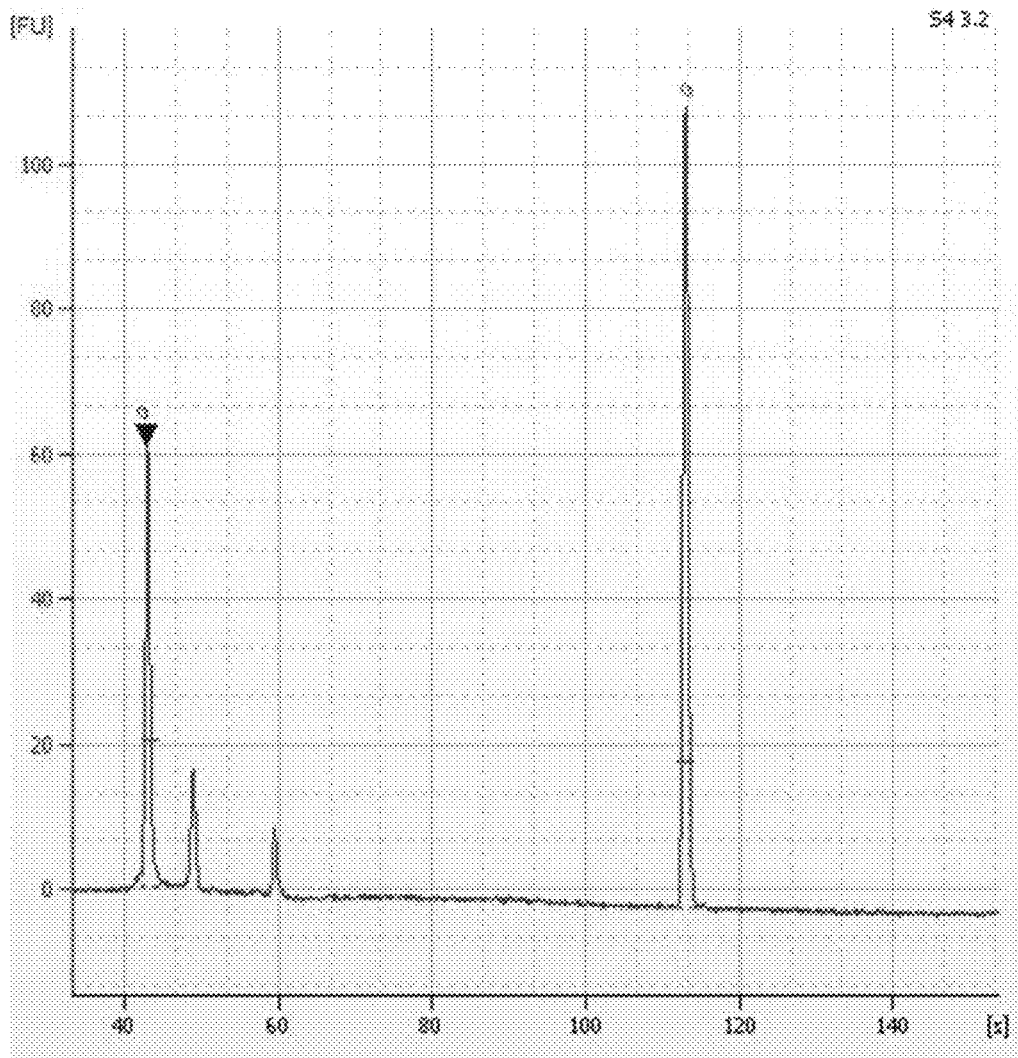
FIG. 38 illustrates a chromatogram trace of ah Agilent Bioanlyser 2100 analysis of the amplified product "c" of FIG. 35. The first peak (15) represents the lower marker with a length of 15 bp. The third peak represents the uppermarker (1500) with a length of 1500 bp. A middle peak is observed for mutant 3.2 but with a low amplitude.

After PCR reactions all reactions were load on the LC90, an electrophoresis system to confirm presence or absence of a specific product. The results of the ACTB assay on all cell lines are illustrated in FIG. 16. The results of the P16_7_14 Assay on ivM, DKO, and NTC cells lines are illustrated in FIG. 17, and the results of the P16_7_14 Assay on all cells lines are illustrated in FIG. 18.

Conclusions

The ACTS assay is positive for all samples tested and all Ct values are of the same order. We can conclude that the samples used are valid.

The P16_7_14 assay is positive on in vitro methylated DNA and negative on DKO.

The non-template control (NTC) is negative, except for one from the 3 triplicates for the ACTB assay which scored positive, most likely due to a contamination.

It can be concluded that HT29 is hypermethylated for P16 using the P16_7_14 assay. Remark that this is not a quantitative assay. These findings are reflected in the Ct-values, Tm-values and the results achieved with caliper electrophoresis on the Caliper LC90.

Results for KRAS on Primary Samples

Primary Samples

| Primary sample | Gene tested |
| --- | --- |
| EK11-229 | KRAS |
| EK11-392 | KRAS |
| EK12-34 | KRAS |
| EK12-5 | KRAS |

Generation of Bisulfite Treated DNA from Primary Samples

The gDNA primary samples were treated using the EZ DNA Methylation Kit from Zymo Research according to the manufacturer's protocol 200 ng of gDNA for every primary sample is converted in BT-DNA in a volume of 50 ul by use of 100 ul of CT Conversion Reagent at 70 degrees for 3 hours, following this incubation, the samples were bound to the supplied columns and 200 ul of desulfonation buffer was added. Desulfonation was carried out at room temperature for 20 minutes. The columns were washed twice and the modified DNA was eluted into 10 ul elution buffer, which results into a final concentration of 20 ng/ul. After the treatment the samples are stored at −80 degrees for further analysis'.

KRAS Assay on Primary Samples

The epigenetic methylation (Epi MET) assay was performed on in vitro methylated KRAS DNA, and the primary samples EK11-229, EK11-392, EK12-34, and EK12-5 using the wild-type KRAS primers (wt) and the mutant KRAS primers (3.1) and (3.2). The results are illustrated in FIGS. 19-38.

Summary

|  | WILD-TYPE | | MUTANT 3.1 | | MUTANT 3.2 | |
| --- | --- | --- | --- | --- | --- | --- |
|  | Ct | Gel | Ct | Gel | Ct | Gel |
| EK11-229 | POS | POS | NEG | NEG | POS | POS |
| EK11-392 | NEG | NEG | NEG | NEG | POS | POS |
| EK12-34 | POS | POS | NEG | NEG | NEG | NEG |
| EK12-5 | POS | POS | NEG | NEG | NEG |  |
| IV M | POS | NEG | NEG | NEG | NEG | NEG |

Conclusion

All of the BT-MUT primers designed for mutation detection on bisulfite converted DNA are specific for bisulfite converted DNA and do not amplify non-converted material. When using the Quantitect mix for the KRAS assay, only the wild-type BT-MUT primers show amplification on IVM and DKO. The mutated versions do not illustrate amplification. The KRAS mutation 3.2 was detected in SW620 cell line. The 3.2 mutation also was detected in the EK11-392 and EK11-229 primary samples.

In the foregoing description, certain terms have been used for brevity, clearness, and understanding. No unnecessary limitations are to be implied therefrom beyond the requirement of the prior art because such terms are used for descriptive purposes and are intended to be broadly construed. The different compositions and method steps described herein may be used alone or in combination with other compositions and method steps. It is to be expected that various equivalents, alternatives and modifications are possible. Citations to a number of non-patent references are made herein. The cited references are incorporated by reference herein in their entireties. In the event that there is an inconsistency between a definition of a term in the specification as compared to a definition of the term in a cited reference, the term should be interpreted based on the definition in the specification.

The invention claimed is:

1. A method for detecting a mutated BRAF target sequence of interest in a DNA-containing sample, the method comprising:
   (a) contacting the DNA-containing sample with a modifying reagent which selectively modifies non-methylated cytosine residues in the DNA to produce detectable modified residues but which does not modify methylated cytosine residues,
   (b) amplifying the modified DNA-containing sample to produce an amplified target sequence using at least one primer that hybridizes specifically to the mutated BRAF target sequence in the modified DNA-containing sample, and
   (c) detecting the amplified target sequence, thereby detecting the mutated BRAF target sequence.

2. The method of claim 1, further comprising detecting methylation status of the BRAF target sequence by amplifying the modified DNA-containing sample to produce an amplified target sequence using at least one at least one primer that hybridizes specifically to a methylated BRAF target sequence in the modified DNA-containing sample, and detecting the amplified target sequence, thereby detecting the methylated BRAF target sequence.

3. The method of claim 1, wherein amplification is performed using a primer that hybridizes specifically to the mutated BRAF target sequence and a primer that hybridizes specifically to methylated BRAF DNA.

4. The method of claim 1, further comprising detecting a mutated KRAS target sequence of interest in the modified DNA-containing sample, the method further comprising amplifying the modified DNA-containing sample to produce an amplified target sequence using at least one primer that hybridizes specifically to the mutated KRAS target sequence in the modified DNA-containing sample, and detecting the amplified target sequence, thereby detecting the mutated KRAS target sequence.

5. The method of claim 1, wherein the modifying reagent comprises a bisulfite salt.

6. The method of claim 1, further comprising sequencing the amplified target sequence.

7. A method for detecting a mutated BRAF gene target sequence of interest in a DNA-containing sample, the method comprising:
   (a) contacting the DNA-containing sample with a modifying reagent which selectively modifies non-methylated cytosine residues in the DNA to produce detectable modified residues but which does not modify methylated cytosine residues,
   (b) amplifying the modified DNA-containing sample to produce an amplified target sequence using a primer pair comprising SEQ ID NO:3 and SEQ ID NO:2; and
   (c) detecting the amplified target sequence, thereby detecting the mutated BRAF gene target sequence.

8. The method of claim 7, further comprising detecting a mutated KRAS target sequence of interest in the modified DNA-containing sample, the method further comprising amplifying the modified DNA-containing sample to produce an amplified target sequence using at least one primer that hybridizes specifically to the mutated KRAS target sequence in the modified DNA-containing sample, and detecting the amplified target sequence, thereby detecting the mutated KRAS target sequence.

9. The method of claim 7, wherein the modifying reagent comprises a bisulfite salt.

10. The method of claim 7, further comprising sequencing the amplified target sequence.

11. A method for detecting at least one mutated BRAF gene target sequence of interest in a DNA-containing sample, the method comprising:
   (a) contacting the DNA-containing sample with a modifying reagent which selectively modifies non-methylated cytosine residues in the DNA to produce detectable modified residues but which does not modify methylated cytosine residues,
   (b) amplifying the modified DNA-containing sample to produce an amplified target sequence using a primer pair comprising SEQ ID NO:3; and
   (c) detecting the amplified target sequence, thereby detecting the mutated BRAF gene target sequence.

12. The method of claim 11, further comprising detecting a mutated KRAS target sequence of interest in the modified DNA-containing sample, the method further comprising amplifying the modified DNA-containing sample to produce an amplified target sequence using at least one primer that hybridizes specifically to the mutated KRAS target sequence in the modified DNA-containing sample, and detecting the amplified target sequence, thereby detecting the mutated KRAS target sequence.

13. The method of claim 11, wherein the modifying reagent comprises a bisulfite salt.

14. The method of claim 11, further comprising sequencing the amplified target sequence.

\* \* \* \* \*